(12) United States Patent
Belisle et al.

(10) Patent No.: US 12,343,702 B2
(45) Date of Patent: Jul. 1, 2025

(54) ANIONIC EXCHANGE-HYDROPHOBIC MIXED MODE CHROMATOGRAPHY RESIN

(71) Applicant: BIO-RAD LABORATORIES, INC., Hercules, CA (US)

(72) Inventors: Christopher Belisle, Walnut Creek, CA (US); Hong Chen, San Ramon, CA (US); Yueping Xu, Albany, CA (US); Jiali Liao, San Ramon, CA (US); Xuemei He, Walnut Creek, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 1133 days.

(21) Appl. No.: 16/978,814

(22) PCT Filed: Mar. 8, 2019

(86) PCT No.: PCT/US2019/021376
§ 371 (c)(1),
(2) Date: Sep. 8, 2020

(87) PCT Pub. No.: WO2019/173731
PCT Pub. Date: Sep. 12, 2019

(65) Prior Publication Data
US 2020/0406232 A1 Dec. 31, 2020

Related U.S. Application Data

(60) Provisional application No. 62/647,202, filed on Mar. 23, 2018, provisional application No. 62/640,430, filed on Mar. 8, 2018.

(51) Int. Cl.
*C07K 1/16* (2006.01)
*B01D 15/38* (2006.01)
*B01J 20/26* (2006.01)
*B01J 20/289* (2006.01)
*B01J 20/30* (2006.01)

(52) U.S. Cl.
CPC ........ *B01J 20/289* (2013.01); *B01D 15/3809* (2013.01); *B01D 15/3847* (2013.01); *B01J 20/265* (2013.01); *B01J 20/3085* (2013.01); *C07K 1/165* (2013.01); *B01J 2220/52* (2013.01)

(58) Field of Classification Search
CPC ........................ B01J 20/3253; B01J 20/3255; B01J 20/3219; B01J 20/289; B01J 20/3085; B01J 20/265; B01J 41/20; B01J 47/014; B01J 20/3285; B01J 2220/52; B01J 20/286; B01D 15/3809; B01D 15/3847; B01D 15/363; B01D 15/327; C07K 1/165; C07K 16/00
See application file for complete search history.

(56) References Cited

U.S. PATENT DOCUMENTS

| | | |
|---|---|---|
| 5,429,746 A | 7/1995 | Shadle et al. |
| 5,645,717 A | 7/1997 | Hjerten et al. |
| 5,647,979 A | 7/1997 | Liao et al. |
| 5,652,348 A | 7/1997 | Burton et al. |
| 5,935,429 A | 8/1999 | Liao et al. |
| 5,945,520 A | 8/1999 | Burton et al. |
| 6,423,666 B1 | 7/2002 | Liao et al. |
| 6,498,236 B1 | 12/2002 | Lihme et al. |
| 7,714,112 B2 | 5/2010 | Engstrand et al. |
| 7,867,784 B2 | 1/2011 | Engstrand et al. |
| 8,748,582 B2 | 6/2014 | Hearn et al. |
| 8,895,710 B2 | 11/2014 | Engstrand et al. |
| 9,169,331 B2 | 10/2015 | Liu et al. |
| 9,309,282 B2 | 4/2016 | Liao et al. |
| 9,486,799 B2 | 11/2016 | Pohl |
| 9,669,402 B2 | 6/2017 | Liao et al. |
| 9,975,920 B2 | 5/2018 | Aldinger et al. |
| 10,287,314 B2 | 5/2019 | Bian et al. |
| 10,457,749 B2 | 10/2019 | Fouque et al. |
| 10,487,138 B2 | 11/2019 | Felföldi et al. |
| 10,682,640 B2 | 6/2020 | Liao et al. |

(Continued)

FOREIGN PATENT DOCUMENTS

| | | |
|---|---|---|
| AU | 200173432 | 5/2002 |
| CN | 101060931 | 10/2007 |

(Continued)

OTHER PUBLICATIONS

PubChem ID 26050, "N,N-Dimethyl-2-phenoxyethanamine" Mar. 26, 2005, pp. 1-14.
Written Opinion in International Application No. PCT/US2019/021376, Jul. 9, 2019, pp. 1-7.
Extended European Search Report for EP 19764738.1, Jul. 30, 2021, pp. 1-13.
Li, Y. et al. "New reversed-phase/anion-exchange/hydrophilic interaction mixed-mode stationary phase based on dendritic polymer-modified porous silica" Journal of Chromatography A, 2014, pp. 133-139, vol. 1337.
De Koning et al., "Crosslinked agarose encapsulated sorbents resistant to steam sterilization. Preparation and mechanical properties" Journal of Biomedical Materials Research, vol. 18, 1984, pp. 1-13.

(Continued)

Primary Examiner — Shafiqul Haq
(74) Attorney, Agent, or Firm — SALIWANCHIK, LLOYD & EISENSCHENK

(57) ABSTRACT

Chromatography resins having anionic exchange-hydrophobic mixed mode ligands, that are useful for purifying target biomolecules using anionic exchange (i.e., where the ligand is positively charged) and hydrophobic mixed mode chromatography. The chromatography resins allow for efficient purification of target biomolecules (e.g., recombinant proteins, antibodies, antibody-drug conjugates, or antibody derivatives including, but not limited to, antibody fragments and antibody fusions) from a sample, and have been found to be useful in purifying monomeric target biomolecules from aggregate target biomolecules. In an embodiment, the chromatography resins are useful for separating antibodies from one or more components (e.g., contaminants) in the sample.

14 Claims, 4 Drawing Sheets

(56) References Cited

U.S. PATENT DOCUMENTS

| | | |
|---|---|---|
| 10,947,268 B2 | 3/2021 | Li et al. |
| 11,305,271 B2 | 4/2022 | Yavorsky et al. |
| 11,896,969 B2 | 2/2024 | Belisle et al. |
| 2006/0052598 A1 | 3/2006 | Burton et al. |
| 2007/0112178 A1 | 5/2007 | Johansson et al. |
| 2007/0244307 A1 | 10/2007 | Engstrand et al. |
| 2009/0270596 A1 | 10/2009 | Gagnon et al. |
| 2011/0139717 A1 | 6/2011 | Malenfant et al. |
| 2011/0266225 A1 | 11/2011 | Johansson et al. |
| 2012/0116027 A1 | 5/2012 | Rasmussen et al. |
| 2012/0259094 A1 | 10/2012 | Hearn et al. |
| 2013/0131318 A1 | 5/2013 | Kremer et al. |
| 2013/0237692 A1 | 9/2013 | Liao et al. |
| 2013/0289247 A1 | 10/2013 | Kremer et al. |
| 2015/0073128 A1 | 3/2015 | Engstrand et al. |
| 2015/0299248 A1 | 10/2015 | Maloisel et al. |
| 2016/0272673 A1 | 9/2016 | Althouse et al. |
| 2017/0232433 A1 | 8/2017 | Liao et al. |
| 2017/0334948 A1 | 11/2017 | Bittermann et al. |
| 2018/0127460 A1 | 5/2018 | Hall et al. |
| 2018/0154281 A1 | 6/2018 | Engstrand et al. |
| 2018/0215786 A1 | 8/2018 | Kozlov et al. |
| 2019/0119415 A1 | 4/2019 | Graalfs |
| 2021/0069692 A1 | 3/2021 | Belisle et al. |

FOREIGN PATENT DOCUMENTS

| | | | |
|---|---|---|---|
| CN | 102762585 | 10/2012 | |
| CN | 103189390 | 7/2013 | |
| CN | 103877748 | 6/2014 | |
| CN | 103998456 | 8/2014 | |
| CN | 109790201 | 5/2019 | |
| WO | 1990012632 A1 | 11/1990 | |
| WO | 1997029825 A1 | 8/1997 | |
| WO | 2006043896 A1 | 4/2006 | |
| WO | WO-2010117598 A2 * | 10/2010 | ............ A61P 37/04 |
| WO | WO 2011/044637 | 4/2011 | |
| WO | WO 2011/104307 | 9/2011 | |
| WO | WO 2013/134251 | 9/2013 | |
| WO | WO 2019/152977 | 8/2019 | |

OTHER PUBLICATIONS

Horejsi, et al.; "The Isolation of Gamma Globulin from Blood-Serum by Rivanol"; Acta Medica Scandinavica; vol. CLV, fasc. I; submitted for publication Mar. 27, 1956; pp. 65-70.

Emöd, et al.; "Five Sepharose-Bound Ligands for the Chromatographic Purification of Clostridium Collagenase and Clostripain"; FEBS Letters; vol. 77, No. 1; May 1977; pp. 51-56.

Miller; "Rivanol, Resin and the Isolation of Thrombins"; Nature; vol. 184; Aug. 8, 1959; p. 450.

Abraham; "Solid-Phase Radioimmunoassay of Estradiol-17β"; Preliminary Communications, The Endocrine Society; vol. 29; Jun. 1969; pp. 865-870.

Te Booy, et al.; "Large-scale purification of factor Vlll by affinity chromatography: optimization of process parameters"; J. of Chromatography; vol. 503; 1990; pp. 103-114.

Te Booy, et al.; "Affinity purification of plasma proteins: characterization of six affinity matrices and their application for the isolation of human factor VIII"; Thromb. Haemost.; vol. 61(2); Apr. 1989; pp. 234-237.

Sato, et al.; "Development of Mammalian Serum Albumin Affinity Purification Media by Peptide Phage Display"; Biotechnol. Prog. vol. 18; Jan. 26, 2002; pp. 182-192.

Anspach; "Endotoxin removal by affinity sorbents"; J. Biochem. Biophys. Methods; vol. 49; 2001; pp. 665-681.

Nemoto, et al.; "Newly Developed Immobilized Polymyxin B Fibers Improve the Survival of Patients with Sepsis"; Blood Purif.; vol. 19; 2001; pp. 361-369.

Jaber, et al.; "Extracorporeal Adsorbent-Based Strategies in Sepsis"; American J of Kidney Diseases; vol. 30, No. 5, Suppl 4; Nov. 1997; pp. S44-S56.

Persson, et al.; "Purification of Antibody and Antibody-Fragment From E. coli Homogenate Using 6,9-Diamino-2-ethoxyacridine Lactate as Precipitation Agent"; Biotechnology and Bioengineering; vol. 87, No. 3, Aug. 5, 2004; pp. 424-434.

Franek; "Purification of IgG Monocloanl Antibodies from Ascitic Fluid Based on Rivanol Precipitation"; Methods in Enzymology; vol. 121; 1986; 631-638.

Simmons, et al.; "Expression of full-length immunoglobulins in *Escherichia coli*: rapid and efficient production of aglycosylated antibodies"; J. of Immunological Methods; vol. 263; Feb. 14, 2002; pp. 133-147.

Petsch, et al.; "Endotoxin removal from protein solutions"; J. of Biotechnology; vol. 76; 2000; pp. 97-119.

Mayer, et al.; "Modifying an immunogenic epitope on a therapeutic protein: a step towards an improved system for antibody-directed enzyme prodrug therapy (ADEPT)"; British J. of Cancer; vol. 90; May 25, 2004; pp. 2402-2410.

Talmadge, et al.; "Efficient Endotoxin Removal with a New Sanitizable Affinity Column; Affi-Prep Polymyxin"; J. of Chromatography; vol. 476; 1989; pp. 175-185.

Elder, et al.; "Evaluation of Quaternary Aminoethy-Sephadex A50 Column Chromatography for Detection of Anti-Cytomegalovirus Immunoglobulin M"; Mayo Clin Proc; vol. 62; May 1987; pp. 345-350.

Fung, et al.; "Serologic Diagnosis of Toxoplasmosis with Emphasis on the Detection of Toxoplasma-specific Immunoglobulin M Antibodies"; American Journal of Clinical Pathology; vol. 83, No. 2; Feb. 1983; pp. 196-199.

Joustra, et al.; "Preparation of Freeze-dried, Monomeric and Immunochemically Pure IgG by a Rapid and Reproducible Chromatographic Technique"; from Protides of the Biological Fluids, Chapter D: Techniques; Published by Elsevier, vol. 17, 1970, pp. 510-515.

Jelezarova, et al.; "Interaction of C3b2-IgG complexes with complement proteins properdin, factor B and factor H: Implications for amplification"; Biochem J.; vol. 349; 2000; pp. 217-223.

Eriksson. K. et al. "MAb Contaminant Removal with a Multimodal Anion Exchanger A Platform Step to Follow Protein A" *BioProcess International*, Feb. 2009, pp. 52-56, vol. 7, No. 2.

European Search Report for EP 19764738.1, May 7, 2021, pp. 1-13.

PubChem CID 37732, Mar. 26, 2005, pp. 1-17.

International Search Report and Written Opinion in International Application No. PCT/US2020/49305, Feb. 5, 2021, pp. 1-11.

\* cited by examiner

ANIONIC EXCHANGE-HYDROPHOBIC MIXED MODE CHROMATOGRAPHY RESIN

CROSS-REFERENCE TO RELATED APPLICATIONS

This application is the U.S. national stage application of International Patent Application No. PCT/US2019/021376, filed Mar. 8, 2019, which claims the benefit of U.S. Provisional Application Ser. Nos. 62/640,430, filed Mar. 8, 2018 and 62/647,202, filed Mar. 23, 2018.

BACKGROUND

The extraction of immunoglobulins from source liquids, which are primarily mammalian bodily fluids or cell culture harvest, is of value in obtaining the immunoglobulins in a sufficiently concentrated or purified form for diagnostic and therapeutic uses as well as laboratory studies in general. Similarly, purification of other types of proteins and other molecules from biological samples can be of value.

SUMMARY

Figure 1:
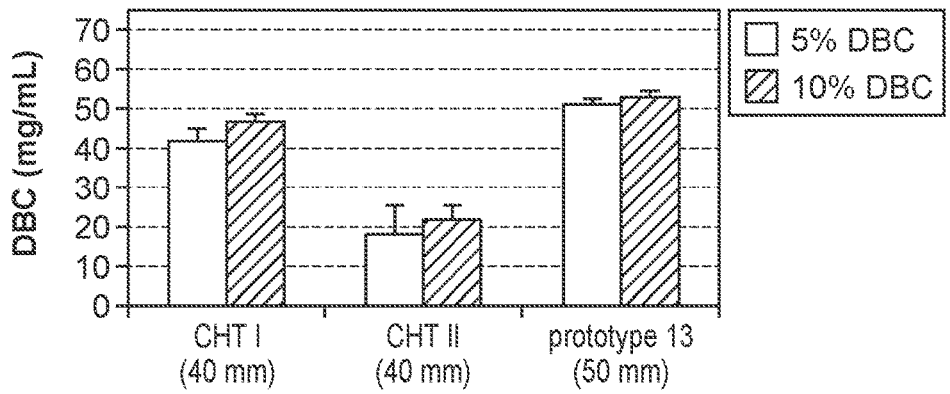
FIG. 1 is the dynamic binding capacity (DBC) for various mixed mode chromatography resins for monoclonal antibody S (mAb S).

Chromatography resins comprising chromatography matrices linked to an anionic exchange-hydrophobic mixed mode ligand are provided. In some embodiments, the chromatography resin has the formula:

Chromatography matrix-(X)—N($R^1$)($R^2$)—($R^3$-L)$_n$-Ar or an anionic salt thereof,
wherein:
X is a spacer;
$R^1$ and $R^2$ are each independently $C_1$ to $C_6$ alkyl optionally substituted with —OH;
$R^3$ is $C_2$ to $C_6$ alkyl or $C_4$ to $C_6$ cycloalkyl;
L is $NR^4$, O, or S, wherein $R^4$ is hydrogen or $C_1$ to $C_4$ alkyl;
n=1 or 2; and
Ar is a 6-10 membered ring and:
  if Ar is aryl, the aryl is optionally substituted with up to five $C_1$ to $C_3$ unsubstituted alkyl, $C_3$ to $C_6$ branched alkyl, unsubstituted aryl, or fluorine groups; or
  if Ar is heteroaryl, the heteroaryl is optionally substituted with up to four alkyl groups.

In some embodiments of the chromatography resin:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$— 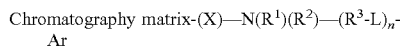 CH$_2$—CH(OH)—CH$_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$— $CH_2$—$CH_2$—O—$CH_2$—CH(OH)—$CH_2$—, and —CO—NH—C($CH_3$)$_2$—CO—;
$R^1$ and $R^2$ are each independently $C_1$ to $C_3$ alkyl;
$R^3$ is $C_2$ to $C_4$ alkyl;
L is O;
n=1; and
Ar is a 6 membered ring and:
  if Ar is aryl, the aryl is optionally substituted with up to four $C_1$ to $C_2$ unsubstituted alkyl, $C_3$ to $C_4$ branched alkyl, or fluorine groups or
  if Ar is heteroaryl, the heteroaryl is optionally substituted with up to three alkyl groups.

DETAILED DESCRIPTION

Provided are chromatography resins that are useful for purifying target biomolecules using anionic exchange (i.e., where the ligand is positively charged) and hydrophobic mixed mode chromatography. The chromatography resins allow for efficient purification of target biomolecules (e.g., recombinant proteins, antibodies, antibody-drug conjugates, or antibody derivatives including, but not limited to, antibody fragments and antibody fusions) from a sample, and have been found to be useful in purifying monomeric target biomolecules from aggregate target biomolecules. In an embodiment, the chromatography resins are useful for separating antibodies from one or more components (e.g., contaminants) in the sample.

Definitions

Unless otherwise stated, the following terms used in this application, including the specification and claims, have the definitions given below. As used in this specification and the appended claims, the singular forms "a", "an", and "the" include plural referents unless the content clearly dictates otherwise. Definition of standard chemistry terms can be found in reference works, including Carey and Sundberg (2007) "Advanced Organic Chemistry 5th Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

"Antibody" refers to an immunoglobulin, composite (e.g., fusion), or fragmentary form thereof. The term includes but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" also includes composite forms including but not limited to fusion proteins containing an immunoglobulin moiety. "Antibody" also includes antibody fragments such as Fab, F(ab')2, Fv, scFv, Fd, dAb, Fc, whether or not they retain antigen-binding function.

As used herein, the term "alkyl" refers to a straight or branched, saturated, aliphatic radical having between 1-10 carbon atoms. For example, $C_1$-$C_6$ alkyl includes, but is not limited to, methyl, ethyl, propyl, isopropyl, butyl, isobutyl, sec-butyl, tert-butyl, pentyl, isopentyl, and/or hexyl. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two chemical groups together.

As used herein, the term "cycloalkyl" refers to monocyclic alkyl having the number of carbon atoms indicated. Monocyclic rings include, for example, cyclobutyl, cyclopentyl, and cyclohexyl.

As used herein, the term "aryl" refers to a monocyclic or fused bicyclic aromatic ring assembly. For example, aryl can be phenyl, naphthyl, or pyridyl. Aryl groups can optionally be substituted by one, two, three, four, or five unsubstituted alkyl groups, unsubstituted aryl groups, or fluorine groups.

The term "heteroatom" refers to N, O and S.

As used herein, the term "heteroaryl group" refers to aromatic groups that include one heteroatom as a ring member. Examples include, but are not limited to, pyrrole, furan, thiophene, and pyridine. Heteroaryl groups can optionally be substituted by one, two, three, or four alkyl groups.

An "anionic salt" is formed at a basic (e.g., alkylamino) group in the ligands. Anionic salts include, but are not limited to, halides, sulfonates, sulfates, carboxylates, phosphates, acetates, citrates and nitrates. Examples of acid-addition salts include, but are not limited to, hydrochloride, hydrobromide, hydroiodide, sulfate, acetate, citrate, and nitrate.

As used herein, the term "spacer" refers to a molecule having 1-30 atoms selected from H, C, N, O and S. The spacer has a neutral charge and can include cyclic groups. The spacer links the chromatographic ligand to the chromatography matrix. The types of bonds used to link the spacer to the chromatography matrix include, but are not limited to, amides, amines, ethers, esters, carbamates, ureas, thioethers, thiocarbamates, thiocarbonate and thioureas. In some embodiments, the bonds used to link the spacer to the chromatography matrix are amines, ethers or amides.

"Biological sample" refers to any composition containing a target molecule of biological origin (a "biomolecule) that is desired to be purified. In some embodiments, the target molecule to be purified is an antibody or a non-antibody protein (e.g., hormones or enzymes).

"Bind-elute mode" refers to an operational approach to chromatography in which the buffer conditions are established so that target molecules and, optionally undesired contaminants, bind to the ligand when the sample is applied to the ligand. Fractionation of the target can be achieved subsequently by changing the conditions such that the target is eluted from the support. In some embodiments, contaminants remain bound following target elution. In some embodiments, contaminants either flow-through or are bound and eluted before elution of the target.

"Flow-through mode" refers to an operational approach to chromatography in which the buffer conditions are established so that the target molecule to be purified flows through the chromatography support comprising the ligand, while at least some sample contaminants are selectively retained, thus achieving their removal from the sample.

Chromatography Resins

In a first embodiment, a chromatography resin has the formula:

Chromatography matrix-(X)—N($R^1$)($R^2$)—($R^3$-L)$_n$-Ar or an anionic salt thereof, wherein:

X is a spacer;

$R^1$ and $R^2$ are each independently $C_1$ to $C_6$ alkyl optionally substituted with —OH;

$R^3$ is $C_2$ to $C_6$ alkyl or $C_4$ to $C_6$ cycloalkyl;

L is $NR^4$, O, or S, wherein $R^4$ is hydrogen or $C_1$ to $C_4$ alkyl;

n is 1 or 2; and

Ar is a 6-10 membered ring and:

if Ar is aryl, the aryl is optionally substituted with up to five $C_1$ to $C_3$ unsubstituted alkyl, $C_3$ to $C_6$ branched alkyl, unsubstituted aryl, or fluorine groups; or if Ar is heteroaryl, the heteroaryl is optionally substituted with up to four alkyl groups.

The nitrogen adjacent to the spacer carries a positive charge as a consequence of its structure and thus the charge is independent of pH. Therefore these resins provide strong ion exchange.

In a first aspect of the first embodiment, $R^1$ and $R^2$ are each independently $C_1$ to $C_3$ alkyl. Alternatively, $R^1$ and $R^2$ are each independently $C_1$ or $C_2$ alkyl.

In a second aspect of the first embodiment, $R^3$ is $C_2$ to $C_4$ alkyl. Alternatively, $R^3$ is $C_2$ or $C_3$ alkyl.

In a third aspect of the first embodiment, L is $NR^4$ or O; or $NR^4$ or S. Alternatively, L is O.

In a fourth aspect of the first embodiment, n is 1.

In a fifth aspect of the first embodiment, Ar is a 6 membered ring and if Ar is aryl, the aryl is optionally substituted with up to four $C_1$ to $C_2$ unsubstituted alkyl, $C_3$ to $C_4$ branched alkyl, or fluorine groups or if Ar is heteroaryl, the heteroaryl is optionally substituted with up to three alkyl groups. Alternatively, Ar is phenyl, naphthyl, or pyridyl optionally substituted with up to three $C_1$ to $C_2$ unsubstituted alkyl or fluorine groups. Alternatively, Ar is phenyl optionally substituted with one or two $C_1$ to $C_2$ unsubstituted alkyl. Alternatively, Ar is unsubstituted phenyl. Alternatively, Ar is heteroaryl and a heteroatom in the heteroaryl is N. Alternatively, Ar is unsubstituted heteroaryl. In yet another alternative, Ar is pyridyl.

In a sixth aspect of the first embodiment, X is attached to chromatography matrix via a bond selected from an amide, amine, ether, ester, carbamate, urea, thioether, thiocarbamate, thiocarbonate and thiourea. Alternatively the bond is an amine, ether or amide.

In an seventh aspect of the first embodiment, X is selected from the group consisting of
—O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—. Alternatively, X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH($CH_2$—OH)—(O—$CH_2$—CH(OH)—$CH_2$)$_2$—.

In a second embodiment, the chromatography resin has the formula:

Chromatography matrix-(X)—N($R^1$)($R^2$)—($R^3$-L)$_n$-Ar or an anionic salt thereof, wherein:
X is selected from the group consisting of —O—CH₂—, —O—CH₂—CH₂—, —O—CH₂—CH₂—CH₂—, —O—CH₂—CH₂—CH₂—CH₂—, —O—CH₂—CH(CH₂—OH)—(O—CH₂—CH(OH)—CH₂)₂—, —O—CH₂—CH₂—CH(CH₂—OH)—(O—CH₂—CH(OH)—CH₂)₂—, —O—CH₂—CH(OH)—CH₂—, —O—CH₂—CH₂—CH(OH)—CH₂—CH₂—, —O—CH₂—CH(OH)—CH₂—O—CH₂—CH₂—CH₂—CH₂—O—CH₂—CH(OH)—CH₂—, and —CO—NH—C(CH₃)₂—CO—;

$R^1$ and $R^2$ are each independently $C_1$ to $C_3$ alkyl;
$R^3$ is $C_2$ to $C_4$ alkyl;
L is O;
n is 1; and
Ar is a 6 membered ring and:
if Ar is aryl, the aryl is optionally substituted with up to four $C_1$ to $C_2$ unsubstituted alkyl, $C_3$ to $C_4$ branched alkyl, or fluorine groups or
if Ar is heteroaryl, the heteroaryl is optionally substituted with up to three alkyl groups.

In a first aspect of the second embodiment, $R^1$ and $R^2$ are each independently $C_1$ or $C_2$ alkyl.

In a second aspect of the second embodiment, $R^3$ is $C_2$ or $C_3$ alkyl.

In a third aspect of the second embodiment, Ar is phenyl, naphthyl, or pyridyl optionally substituted with up to three $C_1$ to $C_2$ unsubstituted alkyl. Alternatively, Ar is phenyl optionally substituted with one or two $C_1$ to $C_2$ unsubstituted alkyl. Alternatively, Ar is unsubstituted phenyl. Alternatively, Ar is heteroaryl and a heteroatom in the heteroaryl is N. Alternatively, Ar is unsubstituted heteroaryl.

In a third embodiment, the chromatography resin has the formula:

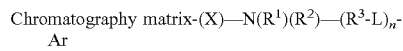

Chromatography matrix-(X)—N($R^1$)($R^2$)—($R^3$-L)$_n$-Ar or an anionic salt thereof,
wherein:
X is selected from the group consisting of —O—CH₂—, —O—CH₂—CH₂—, —O—CH₂—CH₂—CH₂—, —O—CH₂—CH₂—CH₂—CH₂—, and —O—CH₂—CH(CH₂—OH)—(O—CH₂—CH(OH)—CH₂)₂—;
$R^1$ and $R^2$ are each independently $C_1$ or $C_2$ alkyl;
$R^3$ is $C_2$ or $C_3$ alkyl;
L is O;
n is 1; and
Ar is phenyl, naphthyl, or pyridyl optionally substituted with up to three $C_1$ to $C_2$ unsubstituted alkyl.

In a first aspect of the third embodiment, Ar is phenyl optionally substituted with one or two $C_1$ to $C_2$ unsubstituted alkyl. Alternatively, Ar is unsubstituted phenyl.

In a fourth embodiment, —(X)—N($R^1$)($R^2$)—($R^3$-L)$_n$-Ar is any one of the ligands of Table 1.

TABLE 1

| Ligand | Structure of Ligand | Structure of Ligand Attached to Matrix (Spheres represent matrix and Spacer X) | Resin Number |
|---|---|---|---|
| N,N-dimethyl-2-phenoxyethan-1-amine | | | 13 |
| N,N-dimethyl-3-phenoxypropan-1-amine | | | 94 |
| N,N-dimethyl-2-(2-phenoxyethoxy)ethan-1-amine | | | 34-1 |
| 2-(methyl(2-phenoxyethyl)amino)ethan-1-ol | | | 34-2 |
| 2-(3,5-dimethylphenoxy)-N,N-dimethylethan-1-amine | | | 86-1 |

TABLE 1-continued

| Ligand | Structure of Ligand | Structure of Ligand Attached to Matrix (Spheres represent matrix and Spacer X) | Resin Number |
|---|---|---|---|
| 2-([1,1'-biphenyl]-4-yloxy)-N,N-dimethylethan-1-amine | | | 86-2 |
| N,N-dimethyl-2-(p-tolyloxy)ethan-1-amine | | | 97-1 |
| 2-(4-ethylphenoxy)-N,N-dimethylethan-1-amine | | | 97-2 |
| 2-(4-isopropylphenoxy)-N,N-dimethylethan-1-amine | | | 98-1 |
| 2-(4-fluorophenoxy)-N,N-dimethylethan-1-amine | | | 32-1 |
| 2-(2,5-difluorophenoxy)-N,N-dimethylethan-1-amine | | | 91-1 |
| 3-(3,5-difluorophenoxy)-N,N-dimethylpropan-1-amine | | | 91-2 |
| 2-(3-fluorophenoxy)-N,N-dimethylethan-1-amine | | | 91-3 |

TABLE 1-continued

| Ligand | Structure of Ligand | Structure of Ligand Attached to Matrix (Spheres represent matrix and Spacer X) | Resin Number |
|---|---|---|---|
| 2-(3,5-difluorophenoxy)-N,N-dimethylethan-1-amine | | | 91-4 |
| 2-(3,4-difluorophenoxy)-N,N-dimethylethan-1-amine | | | 91-5 |
| N,N-dimethyl-2-(3,4,5-trifluorophenoxy)ethan-1-amine | | | 91-6 |
| 2-(4-(tert-butyl)phenoxy)-N,N-dimethylethan-1-amine | | | 32-2 |
| N,N-dimethyl-2-(naphthalen-1-yloxy)ethan-1-amine | | | CB216 |
| N,N-dimethyl-2-(perfluorophenoxy)ethan-1-amine | | | 50-1 |
| N,N-dimethyl-2-(pyridin-4-yloxy)ethan-1-amine | | | 71-2 |
| N,N-dimethyl-2-(pyridin-3-yloxy)ethan-1-amine | | | 71-4 |

TABLE 1-continued

| Ligand | Structure of Ligand | Structure of Ligand Attached to Matrix (Spheres represent matrix and Spacer X) | Resin Number |
|---|---|---|---|
| 2-((2,6-dimethylpyridin-4-yl)oxy)-N,N-dimethylethan-1-amine | | | 71-3 |
| N,N-dimethyl-3-(pyridin-4-yloxy)propan-1-amine | | | 71-1 |
| N,N-dimethyl-3-phenoxycyclobutan-1-amine | | | |
| N,N-dimethyl-3-phenoxycyclopentan-1-amine | | | |
| N,N-dimethyl-3-phenoxycyclohexan-1-amine | | | |

In a fifth embodiment, the chromatography resin has the formula:

Chromatography matrix-(X)—N($R^1$)—[($R^3$-L)$_n$-Ar]$_2$ or an anionic salt thereof,
wherein:
X is a spacer;
$R^1$ is $C_1$ to $C_6$ alkyl optionally substituted with —OH;
$R^3$ is $C_2$ to $C_6$ alkyl or $C_4$ to $C_6$ cycloalkyl;
L is $NR^4$, O, or S, wherein $R^4$ is hydrogen or $C_1$ to $C_4$ alkyl;
n is 1 or 2; and
Ar is a 6-10 membered ring and:
if Ar is aryl, the aryl is optionally substituted with up to five $C_1$ to $C_3$ unsubstituted alkyl, $C_3$ to $C_6$ branched alkyl, unsubstituted aryl, or fluorine groups; or
if Ar is heteroaryl, the heteroaryl is optionally substituted with up to four alkyl groups.
In a first aspect of the fifth embodiment, $R^1$ is $C_1$ to $C_3$ alkyl. Alternatively, $R^1$ is $C_1$ or $C_2$ alkyl.
In a second aspect of the fifth embodiment, $R^3$ is $C_2$ to $C_4$ alkyl. Alternatively, $R^3$ is $C_2$ or $C_3$ alkyl.
In a third aspect of the fifth embodiment, L is $NR^4$ or O or $NR^4$ or S. Alternatively, L is O.
In a fourth aspect of the fifth embodiment, n is 1.
In a fifth aspect of the fifth embodiment, Ar is a 6 membered ring and if Ar is aryl, the aryl is optionally substituted with up to four $C_1$ to $C_2$ unsubstituted alkyl, $C_3$ to $C_4$ branched alkyl, or fluorine groups or if Ar is heteroaryl, the heteroaryl is optionally substituted with up to three alkyl groups. Alternatively, Ar is phenyl, naphthyl, or pyridyl optionally substituted with up to three $C_1$ to $C_2$ unsubstituted alkyl or fluorine groups. Alternatively, Ar is phenyl optionally substituted with one or two $C_1$ to $C_2$ unsubstituted alkyl. Alternatively, Ar is unsubstituted phenyl. Alternatively, Ar is heteroaryl and a heteroatom in the heteroaryl is N. Alternatively, Ar is unsubstituted heteroaryl.

In a sixth embodiment, the chromatography resin has the formula:

Chromatography matrix-(X)—N($R^1$)—[($R^3$-L)$_n$-Ar]$_2$ or an anionic salt thereof,
wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—;
$R^1$ is $C_1$ to $C_3$ alkyl;
$R^3$ is $C_2$ to $C_4$ alkyl;

L is O;
n=1; and
Ar is a 6 membered ring and:
   if Ar is aryl, the aryl is optionally substituted with up to four $C_1$ to $C_2$ unsubstituted alkyl, $C_3$ to $C_4$ branched alkyl, or fluorine groups or
   if Ar is heteroaryl, the heteroaryl is optionally substituted with up to three alkyl groups.

In a first aspect of the sixth embodiment, $R^1$ is $C_1$ or $C_2$ alkyl.

In a second aspect of the sixth embodiment, $R^3$ is $C_2$ or $C_3$ alkyl.

In a third aspect of the sixth embodiment, Ar is phenyl, naphthyl, or pyridyl optionally substituted with up to three $C_1$ to $C_2$ unsubstituted alkyl. Alternately, Ar is phenyl optionally substituted with one or two $C_1$ to $C_2$ unsubstituted alkyl. Alternately, Ar is unsubstituted. Alternatively, Ar is heteroaryl and a heteroatom in the heteroaryl is N. Alternatively, Ar is unsubstituted heteroaryl.

In a seventh embodiment, the chromatography resin has the formula:

Chromatography matrix-(X)—N($R^1$)—[($R^3$-L)$_n$-Ar]$_2$ or an anionic salt thereof,
wherein:
   X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH($CH_2$—OH)—(O—$CH_2$—CH(OH)—$CH_2$)$_2$—;
$R^1$ is $C_1$ or $C_2$ alkyl;
$R^3$ is $C_2$ or $C_3$ alkyl; and
L is O;
n is 1; and
Ar is phenyl, naphthyl, or pyridyl optionally substituted with up to three $C_1$ to $C_2$ unsubstituted alkyl.

In a first aspect of the seventh embodiment, Ar is phenyl optionally substituted with one or two $C_1$ to $C_2$ unsubstituted alkyl. Alternately, Ar is unsubstituted.

In an eighth embodiment, —(X)—N($R^1$)—[($R^3$-L)$_n$-Ar]$_2$ is any one of the ligands of Table 2.

TABLE 2

| Ligand | Structure of Ligand | Structure of Ligand Attached to Matrix (Spheres represent matrix and Spacer X) |
|---|---|---|
| N-methyl-2-phenoxy-N-(2-phenoxyethyl)ethan-1-amine | | |
| N-methyl-2-(2-phenoxyethoxy)-N-(2-(2-phenoxyethoxy)ethyl)ethan-1-amine | | |
| 2-(bis(2-phenoxyethyl)amino)ethan-1-ol | | |
| 2-(3,5-dimethylphenoxy)-N-(2-(3,5-dimethylphenoxy)ethyl)-N-methylethan-1-amine | | |
| 2-([1,1'-biphenyl]-4-yloxy)-N-(2-([1,1'-biphenyl]-4-yloxy)ethyl)-N-methylethan-1-amine | | |

TABLE 2-continued

| Ligand | Structure of Ligand | Structure of Ligand Attached to Matrix (Spheres represent matrix and Spacer X) |
|---|---|---|
| N-methyl-2-(p-tolyloxy)-N-(2-(p-tolyloxy)ethyl)ethan-1-amine | | |
| 2-(4-ethylphenoxy)-N-(2-(4-ethylphenoxy)ethyl)-N-methylethan-1-amine | | |
| 2-(4-isopropylphenoxy)-N-(2-(4-isopropylphenoxy)ethyl)-N-methylethan-1-amine | | |
| 2-(4-tert-butyl)phenoxy)-N-(2-(4-tert-butyl)phenoxy)ethyl)-N-methylethan-1-amine | | |
| N-methyl-2-(naphthalen-1-yloxy)-N-(2-(naphthalen-1-yloxy)ethyl)ethan-1-amine | | |
| 2-(4-fluorophenoxy)-N-(2-(4-fluorophenoxy)ethyl)-N-methylethan-1-amine | | |

TABLE 2-continued

| Ligand | Structure of Ligand | Structure of Ligand Attached to Matrix (Spheres represent matrix and Spacer X) |
|---|---|---|
| 2-(2,5-difluorophenoxy)-N-(2-(2,5-difluorophenoxy)ethyl)-N-methylethan-1-amine | | |
| 2-(3-fluorophenoxy)-N-(2-(3-fluorophenoxy)ethyl)-N-methylethan-1-amine | | |
| 2-(3,5-difluorophenoxy)-N-(2-(3,5-difluorophenoxy)ethyl)-N-methylethan-1-amine | | |
| 2-(3,4-difluorophenoxy)-N-(2-(3,4-difluorophenoxy)ethyl)-N-methylethan-1-amine | | |
| N-methyl-2-(3,4,5-trifluorophenoxy)-N-(2-(3,4,5-trifluorophenoxy)ethyl)ethan-1-amine | | |

TABLE 2-continued

| Ligand | Structure of Ligand | Structure of Ligand Attached to Matrix (Spheres represent matrix and Spacer X) |
|---|---|---|
| N-methyl-2-(perfluorophenoxy)-N-(2-(perfluorophenoxy)ethyl)ethan-1-amine | | |
| 2-((2,6-dimethylpyridin-4-yl)oxy)-N-(2-((2,6-dimethylpyridin-4-yl)oxy)ethyl)-N-methylethan-1-amine | | |
| N-methyl-2-(pyridin-4-yloxy)-N-(2-(pyridin-4-yloxy)ethyl)ethan-1-amine | | |
| N-methyl-2-(pyridin-3-yloxy)-N-(2-(pyridin-3-yloxy)ethyl)ethan-1-amine | | |
| N-methyl-3-phenoxy-N-(3-phenoxycyclobutyl)cyclobutan-1-amine | | |

TABLE 2-continued

| Ligand | Structure of Ligand | Structure of Ligand Attached to Matrix (Spheres represent matrix and Spacer X) |
|---|---|---|
| N-methyl-3-phenoxy-N-(3-phenoxycyclopentyl)cyclopentan-1-amine | | |
| N-methyl-4-phenoxy-N-(4-phenoxycyclohexyl)cyclohexan-1-amine | | |

In some embodiments, the anionic salt is hydrochloride or sulfate.

The chromatography matrix is a polymer that is functionalized so that a bond can be formed to the spacer, X. Preferably, the polymer is a hydrophilic polymer. The polymer is insoluble in water. Suitable polymers are polyhydroxy polymers, e.g. based on polysaccharides, such as agarose, dextran, cellulose, starch, pullulan, and completely synthetic polymers, such as polyacrylic amide, polymethacrylic amide, poly(hydroxyalkylvinyl ethers), poly(hydroxyalkylacrylates) and polymethacrylates (e.g. polyglycidylmethacrylate), polyvinyl alcohols and polymers based on styrenes and divinylbenzenes, and copolymers in which two or more of the monomers corresponding to the abovementioned polymers are included. Suitable synthetic polymers include, but are not limited to, Fractogel from TosoHaas, POROS media from ThermoFisher Scientific, Bio-Gel P and Macro Prep from Bio-Rad, HEMA and Separon from TESSEK, and Hyper D and Trisacryl media from Pall. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on copolymers of monovinyl and divinylbenzenes) by polymerisation of monomers exhibiting groups which can be converted to a hydroxyl group, or by hydrophilization of the final polymer, e.g. by adsorption of suitable compounds, such as hydrophilic polymers. Examples of monomers that can be polymerized to achieve useful matrices are vinyl acetate, vinyl propylamine, acrylic acid, methacrylate, butyl acrylate, acrylamide, methacrylamide, vinyl pyrrolidone (vinyl pyrrolidinone), with functional groups in some cases. Cross-linking agents are also of use in many embodiments, and when present can in some embodiments constitute a mole ratio of from about 0.1 to about 0.7 relative to total monomer. Examples of crosslinking agents are dihydroxyethylenebisacrylamide, diallyltartardiamide, triallyl citric triamide, ethylene diacrylate, bisacrylylcystamine, N,N'-methylenebisacrylamide, and piperazine diacrylamide. In some embodiments, the matrix is an UNOsphere™ Support, a polymer produced from water-soluble hydrophilic monomers (Bio-Rad, Hercules, Calif.).

The chromatography matrix can be in the form of a particle, chips, a membrane, or a monolith, i.e., a single block, pellet, or slab of material. Preferably, the chromatography matrix is porous. Particles when used as matrices can be spheres or beads and are either smooth-surfaced or with a rough or textured surface. In some cases, some of the pores are through-pores, extending through the particles to serve as channels large enough to permit hydrodynamic flow or fast diffusion through the pores. When in the form of spheres or beads, the median particle diameter, where the term "diameter" refers to the longest exterior dimension of the particle, is about 25 microns to about 150 microns. Disclosures of exemplary matrices and the processes by which they are made are found in Lihme et al., U.S. Pat. No. 6,498,236, Hjerten et al., U.S. Pat. No. 5,645,717, Liao et al., U.S. Pat. No. 5,647,979, Liao et al., U.S. Pat. No. 5,935,429, and Liao et al., U.S. Pat. No. 6,423,666.

The ligands are linked to the chromatography matrix via the spacer X. Linkage to the chromatography matrix will depend on the specific chromatography matrix used and the chemical group to be linked to the chromatography matrix. Ligands can be linked to the chromatography matrix by performing a reaction between the ligand and a functional group on the chromatography matrix. For chromatography matrices that do not have a suitable functional group, the chromatography matrix is reacted with a suitable activating reagent to create a suitable functional group to which the ligand can be attached. Reductive amination, epoxide chemistry or azlactone chemistry are examples of chemistries acting on aldehyde, epoxide, or azalactone functional groups, respectively.

In some embodiments, the chromatography matrix comprises an epoxide group and a tertiary amine in the ligand is linked to the epoxide group via epoxide chemistry by the scheme below. In this scheme, the spacer X is —O—CH$_2$—CH(OH)—CH$_2$—. In this and other synthetic schemes in this disclosure, the square represents the matrix and all coupling chemistry is shown separately.

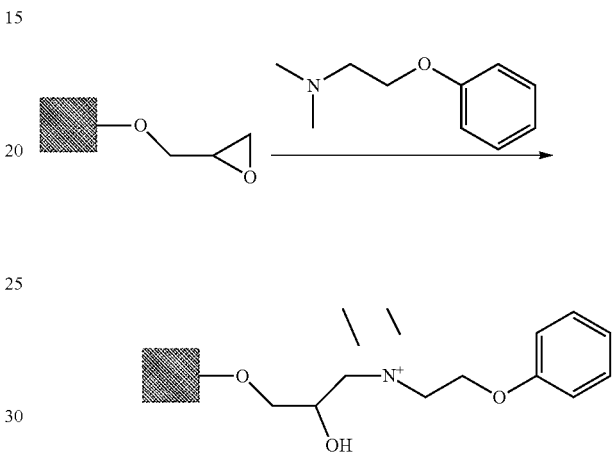

In some embodiments, the chromatography matrix comprises an azlactone ring and a primary amine in the ligand is linked to the azlactone ring by the scheme below. In this scheme, the spacer X is —CO—NH—C(CH$_3$)$_2$—CO—.

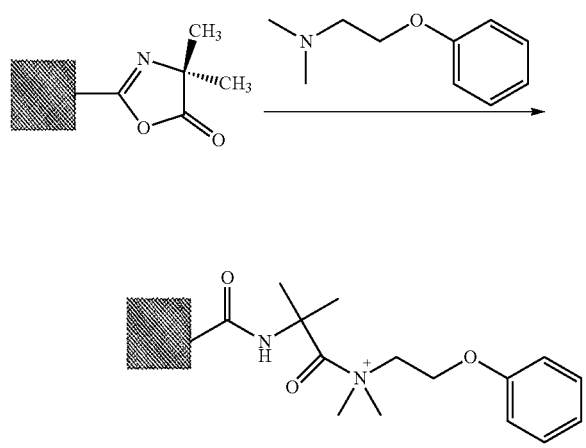

In some embodiments, the chromatography matrix comprises a diol and a tertiary amine is linked to an —OH group by activating the resin with two activating reagents, allylglydicylether (AGE) and bromine, by the scheme below. In this scheme, the spacer X is —O—CH$_2$—CH(CH$_2$—OH)—(O—CH$_2$—CH(OH)—CH$_2$)$_2$—.

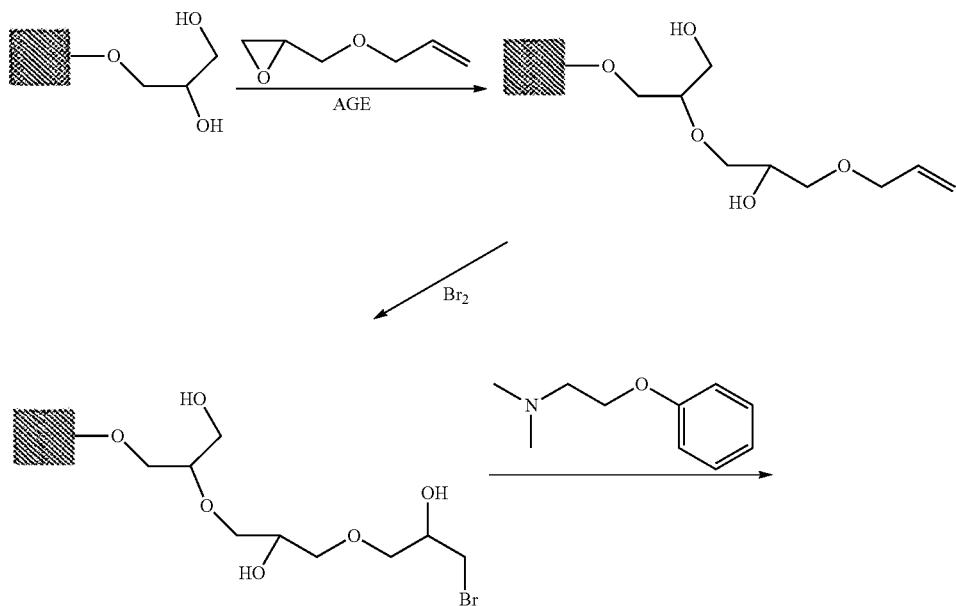

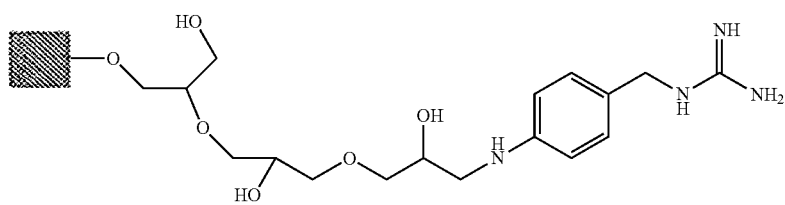

In certain embodiments, the chromatography matrix comprises an —OH group and a tertiary amine is linked to the —OH group by activating the resin with epichlorohydrin by the scheme below. In this scheme, the spacer X is —O—CH$_2$—CH(OH)—CH$_2$—.

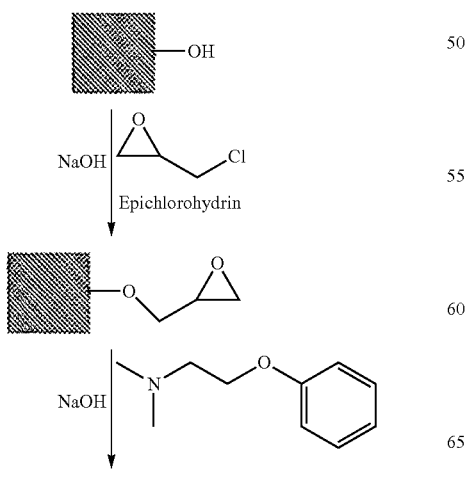

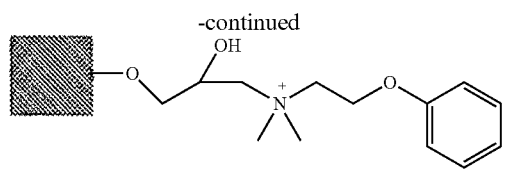

In some embodiments, the chromatography matrix comprises an —OH group and a tertiary amine is linked to the —OH group by activating the resin with 1,4 butanediol-diglycidyl ether by the scheme below. In this scheme, the spacer X is —O—CH$_2$—CH(OH)—CH$_2$—O—CH$_2$—CH$_2$—CH$_2$—CH$_2$—O—CH$_2$—CH(OH)—CH$_2$—.

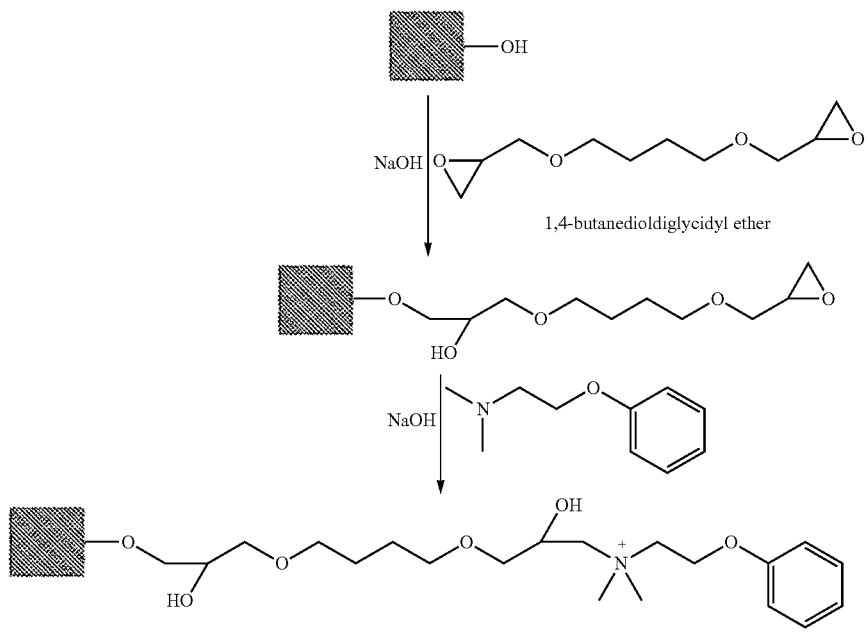

1,4-butanedioldiglycidyl ether

Other activating reagents include, but are not limited to, epibromohydrin (reacts with an —OH functional group on the chromatography matrix to create an epoxide group), poly(ethylene glycol) diglycidyl ether (reacts with an —OH functional group on the chromatography matrix to create an epoxide group), and sulfonyl chlorides such as tosyl chlorides and tresyl chlorides (react with an —OH functional group on the chromatography matrix to create a sulfonate ester).

Other spacers can include, but are not limited to, —O—CH$_2$—, —O—CH$_2$—CH$_2$—CH$_2$—, —O—CH$_2$—CH$_2$—CH$_2$—CH$_2$—, —O—CH$_2$—CH$_2$—CH(CH$_2$—OH)—(O—CH$_2$—CH$_2$—CH(OH)—CH$_2$)$_2$—, and —O—CH$_2$—CH$_2$—CH(OH)—CH$_2$—CH$_2$—.

The chromatography matrix can be utilized in any conventional configuration, including packed columns and fluidized or expanded-bed columns, monoliths or porous membranes, and by any conventional method, including batchwise modes for loading, washes, and elution, as well as continuous or flow-through modes. In some embodiments, a column can range in diameter from 1 cm to 1 m, and in height from 1 cm to 30 cm or more.

Methods

Also provided are methods of purifying a target biomolecule. In an embodiment, the method comprises contacting a sample comprising the biomolecule to a chromatography resin, thereby separating the biomolecule from a contaminant. The resulting purified biomolecule is subsequently collected. In some embodiments, the target biomolecule is a monomeric antibody and the method comprises purifying the monomeric antibody from aggregated antibodies in the sample.

The chromatography resins are useful for purifying target biomolecules using anionic exchange (i.e., where the ligand is positively charged) and hydrophobic mixed mode chromatography. The conditions can be adjusted so as to run the chromatography in bind-elute mode or flow-through mode.

Protein preparations to which the methods can be applied can include unpurified or partially purified antibodies (e.g. IgG) from natural, synthetic, or recombinant sources. Unpurified antibody preparations, for example, can come from various sources including, but not limited to, plasma, serum, ascites fluid, milk, plant extracts, bacterial lysates, yeast lysates, or conditioned cell culture media. Partially purified protein preparations can come from unpurified preparations that have been processed by at least one chromatography, precipitation, other fractionation step, or any combination of the foregoing. In some embodiments, the chromatography step or steps employ any method, including but not limited to size exclusion, affinity, anion exchange, cation exchange, protein A affinity, hydrophobic interaction, immobilized metal affinity chromatography, or hydroxyapatite chromatography. The precipitation step or steps can include salt or polyethylene glycol (PEG) precipitation, or precipitation with organic acids, organic bases, or other agents. Other fractionation steps can include but are not limited to crystallization, liquid:liquid partitioning, or membrane filtration.

As will be appreciated in the art, load, wash and elution conditions for use in the mixed mode chromatography will depend on the specific chromatography media/ligands used.

In some bind-elute mode embodiments, loading (i.e., binding the antibodies to the chromatography resin), and optionally washing, is performed at a pH above 7, e.g., between 7-8, 7-9, etc. Some exemplary bind-elute conditions are:

binding condition: 0-1000 mM NaCl or 100-300 mM NaCl, pH 6.5-8.5 in an appropriate buffer (e.g., Tris, Bis-Tris or phosphate);

elution condition: 1-1000 mM NaCl or 0-150 mM NaCl, pH 3-8.5 or 4.0-6.0, using an appropriate buffer having sodium acetate, citrate, arginine, or glycine.

Optionally, the chromatography resin can be washed under conditions such that some components of the sample are removed from the chromatography resin but the target biomolecules remain immobilized on the chromatography resin. In some embodiments, the target biomolecule is subsequently eluted by changing (e.g., decreasing or increasing) the salt concentration and/or reducing the pH of the solution in contact with the matrix.

Alternatively, the sample can be applied in flow through mode in which some components of the sample are immobilized to the chromatography resin but the target biomolecules flow through (i.e., flow passed) the chromatography resin, and are collected. Some exemplary flow through conditions are 0-150 mM NaCl, pH 4.0-8.0; appropriate buffers can include, e.g., 2-(N-morpholino)ethanesulfonic acid (MES), Bis-Tris, sodium acetate or citrate-phosphate.

EXAMPLES

The following examples are provided by way of illustration only and not by way of limitation. Those of skill in the art will readily recognize a variety of non-critical parameters that could be changed or modified to yield essentially the same or similar results.

Example 1—Preparation of Chromatography Matrices Having the Ligands of Table 1

Reaction with AGE (allylglydicylether): For all the ligands in Table 2, UNOspherem™ Diol (100 mL), a copolymer of 3-allyloxy-1,2-propanediol and vinyl pyrrolidinone, crosslinked with N,N'-methylenebisacrylamide and with a diol density of 200-300 µmol/mL, was used in the form of spherical beads. The beads were suspended in 30 mL of water, 30 mL ION NaOH and 16 g $Na_2SO_4$ at 50° C. in a 250 RPM shaker for 10 min. 100 mL AGE was added and the mixture was kept at 50° C. in the same shaker overnight. The resulting resin was washed with 3×2 column volumes (CV) of isopropyl alcohol (IPA) and 30 CV water.

Bromination: The above AGE modified resin was mixed with 100 mL water and 3.4 g NaOAC. Bromine liquid was added drop-wise to the slurry until an orange color remained (indicating the completion of reaction between double bond and bromine). $Na_2SO_3$ was then added until the orange color disappeared (reduction of excess bromine to bromide). The resin was washed with 30 CV water and was ready for ligand coupling.

Coupling of prototype ligands to UNO sphere Diol bromide: For each prototype ligand (i.e., 16 ligands), 100 mL UNOsphere Diol bromide was mixed with 50 mL water and 50 mL IPA. Then 12.5 g prototype ligand was added. Each mixture was incubated at 50° C. in a 250 RPM shaker overnight. At the end of the reaction, the resin was washed with 2 CV IPA, 2 CV water, 2 CV 1N HCl, 2 CV water, 2 CV 1N NaOH, and then 30 CV water to obtain each prototype resin.

The number, structure, and the density of each ligand attached to UNOsphere Diol bromide resin is listed in Table 3.

TABLE 3

| Resin Number from Table 1 | Structure of Ligand Attached to Matrix (Spheres represent matrix and Spacer X) | Ligand Density (µmol/mL) |
|---|---|---|
| 13 | | 100 |
| 94 | | 113 |
| 34-1 | | 92 |
| 34-2 | | 73 |
| 86-1 | | 86 |

TABLE 3-continued
| Resin Number from Table 1 | Structure of Ligand Attached to Matrix (Spheres represent matrix and Spacer X) | Ligand Density (μmol/mL) |
|---|---|---|
| 86-2 | 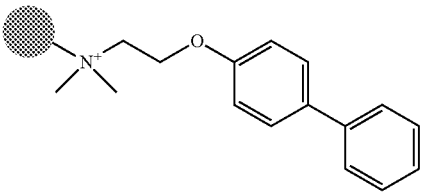 | 64 |
| 97-1 | 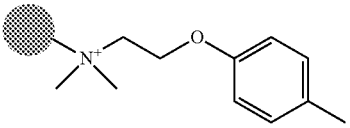 | 108 |
| 97-2 | 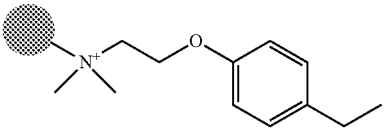 | 102 |
| 98-1 | 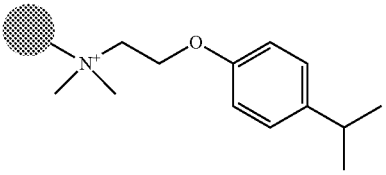 | 69 |
| 32-1 | 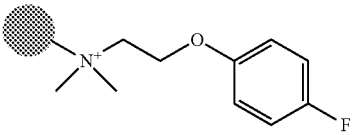 | 102 |
| 91-1 | 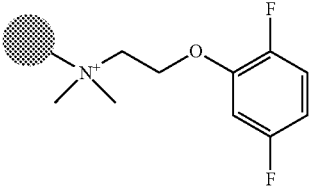 | 73 |
| 91-2 | 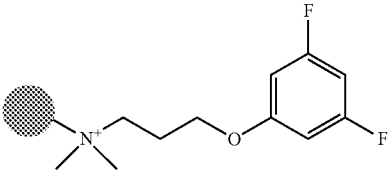 | 103 |
| 91-3 | 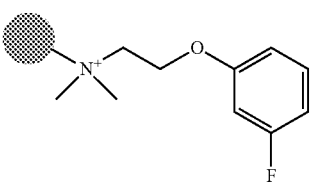 | 109 |

TABLE 3-continued

| Resin Number from Table 1 | Structure of Ligand Attached to Matrix (Spheres represent matrix and Spacer X) | Ligand Density (μmol/mL) |
|---|---|---|
| 91-4 | | 102 |
| 91-5 | | 112 |
| 91-6 | | 112 |
| 32-2 | | 83 |
| 50-1 | | 53 |
| 71-2 | | 46 |
| 71-4 | | 108 |
| 71-3 | | 87 |
| 71-1 | | 86 |

Example 2—Preparation of Chromatography Resin with 2-Phenoxyethylamine as a Comparative Ligand (Prototype 12)

A chromatography resin with Prototype 12 ligand was prepared for comparison purposes. The ligand, 2-phenoxyethylamine, has the following structure:

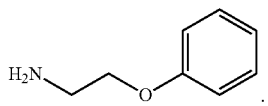

The nitrogen of Prototype 12 can be protonated and thus positively charged based on pH and is thus a weak ion exchanger in contrast to the strong ion exchange ligands of the disclosure.

To attach 2-phenoxyethylamine to UNOsphere™ Diol (20 mL), 82 mol/mL of the chromatography matrix was used in the form of spherical beads. UNOsphere™ Diol is a copolymer of 3-allyloxy-1, 2-propanediol and vinyl pyrrolidinone, crosslinked with N,N'-methylenebisacrylamide and with a diol density of 200-300 μmol/mL.

The beads were suspended in 20 mL of either 0.1 M sodium acetate or water. Sodium periodate was added to a concentration within the range of 50 to 100 mM, and the resulting mixture was incubated at room temperature (approximately 70° F. (21° C.)) for 3-24 hours. The reaction resulted in conversion of the diol groups to aldehyde groups in the range of 150-250 μmol/mL. The resulting aldehyde-functionalized resin was transferred to a 20 mL column where it was washed with 100 mL of water.

Twenty milliliters of UNOsphere aldehyde resin was then suspended in 20 ml of 0.20 M sodium phosphate containing 0.6 g of 2-phenoxyethylamine at pH 7.0. After this mixture was incubated (shaking, 200 rpm) at room temperature for 15 minutes, 200 mg NaBH$_3$CN was then added and the reaction was allowed to continue for 3-20 hours. The 2-phenoxyethylamine concentration in the reaction was determined to be in the range of 25-200 mM. At the end of the reaction, resin prototype 12 was transferred to a 20 ml column, washed with 3 CV of water followed by 1-2 CV of 0.1N HCl, and then washed with 5 CV water. The 2-phenoxyethylamine ligand density was in the range of 25-100 μmol/ml.

Example 3—Resin Evaluation in Bind-Elute Mode

Dynamic binding capacity (DBC) and recovery of an acidic mAb, mAb S (pI~7.2) was determined for three mixed mode resins including two commercial resins and prototype resin 13.

Materials

1. Chromatography media: Ceramic Hydroxyapatite (CHT) Type I (Bio-Rad, 40 μm bead size), CHT Type II (Bio-Rad, 40 μm bead size), and Prototype 13 (Bio-Rad, 50 μm bead size).
2. Test protein monoclonal antibody S (mAb S): Purified from tissue culture fluid with UNOsphere SUPrA™ affinity chromatography media (Bio-Rad), about 25% of mAb S molecules existed as aggregates.
3. Packed columns: Bio-Scale Mini cartridge (Bio-Rad), 0.56×4 cm, about 1 ml bed volume with 0.63 g CHT I and II without compression, or 1 mL of Prototype 13 with a compression factor of 1.2.
4. Binding buffer for CHT I and II: 5 mM NaPO4, 25 mM NaCl, pH 6.5.
5. Binding buffer for Prototype 13: 20 mM NaPO4, pH 7.8.
6. Elution buffer for CHT I and II: 5 mM NaPO4, 550 mM NaCl, pH 6.5.
7. Elution buffer for Prototype 13: 20 mM NaOAc, pH6.0.
8. Stripping buffer: 20 mM NaOAc, pH 4.0.
9. BioLogic Duoflow 10 system (Bio-Rad).

Methods

DBC determination on a BioLogic Duoflow 10 (Bio-Rad): A solution containing about 1.0 mg/mL mAb S in binding buffer was applied onto each column at a flow rate of 0.62 mL/min. For each column, the time at which the column effluent optical density at 280 nm (OD280) reached a value equal to 5 or 10% of the OD280 of the original mAb solution (i.e., the 5 or 10% "breakthrough") was determined. When 5 or 10% breakthrough was reached, sample loading was stopped. The column was then washed with binding buffer. DBC was determined by multiplying the retention time at 5 or 10% breakthrough by the flow rate and mAb concentration.

Target mAb recovery: A solution containing about 1.0 mg/mL of mAb S in binding buffer was injected onto a 1-mL column of resin. The mAb S was eluted with elution buffer at pH 6.0. The collected antibody elution fractions of each column were analyzed by size exclusion high performance liquid chromatography (HPLC-SEC) to determine the percent aggregate content of antibody in the elution fractions. The percent monomer, dimer, and tetramer content for the samples was determined by integrating the respective monomer, dimer, and tetramer peak areas and is listed in Table 4.

Figure 2:
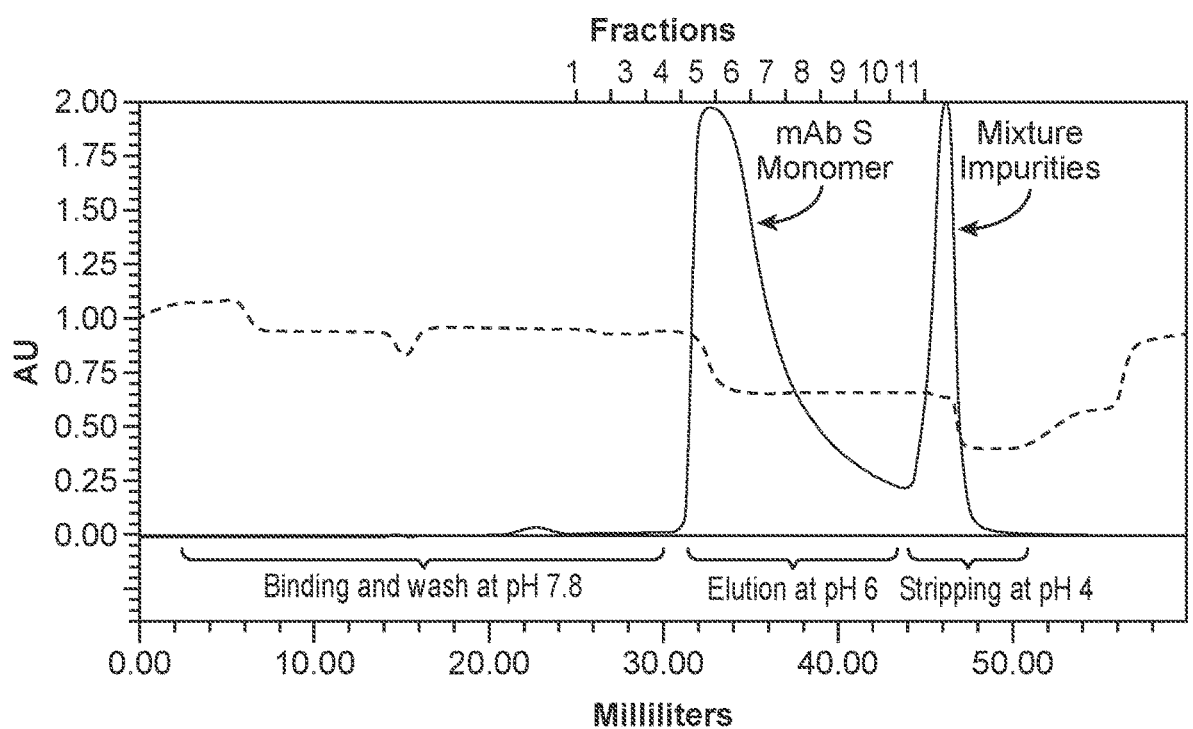
FIG. 2 is the chromatographic elution profile of mAb S from Prototype 13.

Results: The results for dynamic binding capacity (DBC) are shown in FIG. 1, the chromatographic elution profile of mAb S from the resin is shown in FIG. 2, and the monomer content of load, eluate, and strip fractions is in Table 4.

TABLE 4

Monomer Content of mAB S from Prototype 13 Resin

| Sample | Monomer (%) | Dimer (%) | Tetramer (%) |
| --- | --- | --- | --- |
| Load | 93.1 | 6.5 | 0.4 |
| Eluate | 100 | 0 | 0 |
| Strip | 76.8 | 23.2 | 0 |

Referring to FIG. 1, the DBC of Prototype 13 for mAb S is higher than the DBC of CHT I and CHT II.

Referring to Table 4 and FIG. 2, mAb S monomer was eluted from Prototype 13 at about pH 6 (FIG. 2). Thus, Prototype 13 can be used to remove aggregates from mAb S in bind-elute mode.

Example 4—Evaluation of Prototype 13 Resin in Flow Through Mode

Materials
1. Chromatography media: Prototype 13 (Bio-Rad, 50 μm bead size).
2. Sample containing monoclonal antibody T (mAb T): pI of mAb T is about 8.45 (DrugBank DB00072). The mAb T starting material contained 98.3 98.9% monomer when purified from CHO cell culture harvest with UNOsphere SuprA. The mAb T concentration of 24-26 mg/mL was determined by Bradford using bovine IgG as a standard. The starting material had 1-2 ng dsDNA and 150-200 ng/mg host cell protein (HCP) as determined by CHO-CM HCP ELISA kit (Cygnus Technologies).

3. Packed columns: Bio-Scale Mini cartridge (Bio-Rad), 0.56×4 cm, 1 mL of Prototype 13 with a compression factor of 1.2.

4. Binding buffer: 20 mM NaPO4, 100 mM NaCl, pH 6.5.

5. Stripping buffer: 20 mM NaOAc, pH 4.0.

Methods: The resin was packed into a column and was equilibrated with binding buffer. A solution containing 24-26 mg/mL mAb T was applied to the column at a flow rate of 0.62 mL/minute. The mAb T flowed through the column. Stripping buffer was then applied to the column to remove bound substances.

Figure 3:
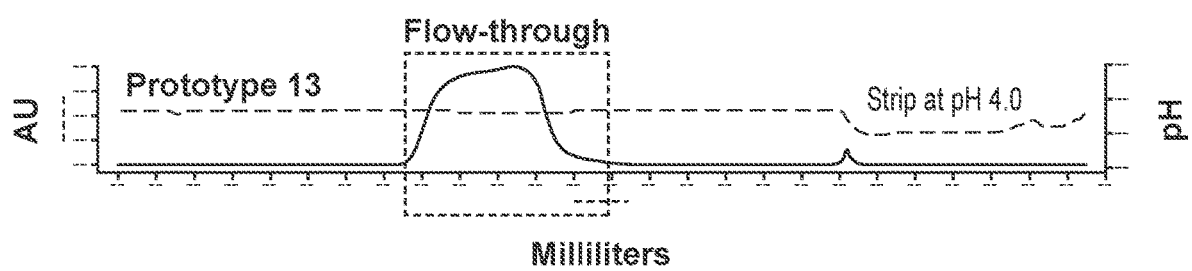
FIG. 3 shows a flow-through mode purification chromatogram of monoclonal antibody T (mAb T) on Prototype 13.

Results: A chromatogram for the resin is shown in FIG. 3. Prior to applying stripping buffer to the column, an increase in OD280 was observed in the chromatogram, indicating that a portion of the mAb T bound to the resin. The results show that Prototype 13 resin can be used to purify mAb T in flow-through mode.

Example 5—Testing of Prototype 13 for mAb Aggregate Removal in Flow Through Mode Materials: The same materials as in Example 4 were used in this experiment.

Methods: The resin was packed into a column and was equilibrated with binding buffer. A solution containing 24-26 mg/mL mAb T was applied to the column at a flow rate of 0.62 mL/minute. The mAb T flowed through the column. Stripping buffer was then applied to the column to remove bound substances. Monomeric mAb T recovered in eluate was quantified by OD280, an absorption efficiency of 1.4 and the following equation:

Monomer Recovery (%)=(Total monomer in eluate/ Total loaded monomer)×100.

Results: The results are shown in Table 5 below. Recovery of the mAb T was the highest with prototype 13 resin at pH 6.5. The results show that prototype 13 resin can be used to purify mAb T in flow-through mode.

TABLE 5 mAb T Recovery

| Media | Monomer Content (%) | Flow Through Monomer Recovery (%) | HCP (ng/mg) | dsDNA (ng/mg) |
|---|---|---|---|---|
| Prototype 13 Flow-through at pH 7.5 | 99.4 | 85.9 | 5.2 | 0 |
| Prototype 13 Flow-through at pH 6.5 | 99.3 | 94.1 | 4.0 | 0 |

Example 6—Testing of Prototype Resins for mAb Aggregate Removal in Bind-Elute Mode Materials 1. Chromatography media: each of the prototype resins listed in Table 3.
2. Test protein mAb S: Purified from tissue culture fluid with UNOsphere SUPrA™ affinity chromatography media (Bio-Rad), about 25% of mAb S molecules existed as aggregates.
3. Packed columns: Bio-Scale Mini cartridge (Bio-Rad), 0.56×4 cm, ~1 ml bed volume with 0.63 g CHT, or 1 mL of Prototype 13 with a compression factor of 1.2.
4. Binding buffer: 20 mM sodium phosphate, pH 7.8.
5. Elution buffer: 20 mM sodium acetate (pH4.0).

Methods

Target mAb recovery: A solution containing about 1.0 mg/mL of mAb S in binding buffer was injected onto a 1-mL column of each of the prototype resins listed in Table 3. The flow rate was 150 cm per hour. The mAb S was eluted with a gradient of 0-100% elution buffer in 10 column volumes. The collected antibody elution fractions of each column were analyzed by size exclusion high performance liquid chromatography (HPLC-SEC) to determine the percent aggregate content of antibody in the elution fractions. The percent monomer content for the samples was determined by subtracting the percent aggregate content from 10000 and is listed in Table 6. Monomeric mAb S recovered in eluates was quantified by OD280, an absorption efficiency of 1.4 and the following equation:

Monomer Recovery (%)=(Total protein in eluate/ Total loaded protein)×100.

Results: The eluate monomer content and monomer recovery results for mAb S are listed in Table 6 for each prototype resin. The data show that each of the resins can be used to recover (or purify) monomeric mAb S.

TABLE 6

Prototype Resin mAb S Monomer Recovery

| Prototype Resin | Eluate Monomer Content (%) | Monomer Recovery (%) |
|---|---|---|
| 13 | 83.4 | 96.5 |
| 94 | 94.0 | 80.0 |
| 34-2 | 84.2 | 89.8 |
| 34-1 | 79.5 | 80.7 |
| 97-1 | 92.4 | 100 |
| 97-2 | 99.0 | 94.3 |
| 98-1 | 100 | 75.6 |
| 86-1 | 100 | 61.9 |
| 86-2 | 100 | 17.7 |
| 32-2 | 100 | 68.5 |
| 32-1 | 84.8 | 89.5 |
| 91-1 | 87.2 | 90.0 |
| 91-2 | 97.2 | 53.7 |
| 91-3 | 97.1 | 67.1 |
| 91-4 | 97.6 | 63.2 |
| 91-5 | 97.8 | 75.3 |
| 91-6 | 97.5 | 77.6 |
| 50-1 | 78.2 | 100 |
| 71-1 | 0 (100% in flow through) | 0 |
| 71-2 | 0 (100% in flow through) | 0 |
| 71-3 | 50 | 68.9 |
| 71-4 | 68 | 85.7 |

Example 7—Comparison of Prototype 12 and Prototype 13 Resins in Bind-Elute Mode

Materials and Methods

Target mAb recovery: A solution containing 1.18 mg/mL of mAb S in binding buffer (20 mM sodium phosphate, pH7.8) was injected onto a 1-mL column of each of the prototype resins 12 and 13. The flow rate was 150 cm per hour. The mAb S was eluted with a gradient of 0-100% elution buffer (20 mM sodium acetate, pH4.0) in 10 column volumes. The collected antibody elution fractions of each column were analyzed by size exclusion high performance liquid chromatography (HPLC-SEC) to determine the percent monomer and aggregate content of antibody in the elution fractions. The percent monomer, dimer, and tetramer content for the samples with each resin was determined by integrating the respective monomer, dimer, and tetramer peak areas and is listed in Tables 7 and 8.

Results: The monomer content results for monomeric mAb S with the two resins are listed in Tables 7 and 8.

TABLE 7

Monomer Recovery of mAb S with Prototype 12

| Sample | Time range (min) | Monomer Content (%) | Dimer (%) | Tetramer (%) |
|---|---|---|---|---|
| Starting Material | — | 74.1 | 20.3 | 5.6 |
| Flow Through | 45-64 | 96.2 | 3.8 | 0 |
| Eluate 1 | 74-77 | 77.5 | 19.3 | 3.2 |
| Eluate 2 | 77-80 | 70.3 | 23.2 | 3.5 |
| Eluate 3 | 80-82 | 69.9 | 22.9 | 7.2 |
| Combined Eluates 1 to 3 | 74-82 | 72.8 | 22.8 | 4.4 |

TABLE 8

Monomer Recovery of mAb S with Prototype 13

| Sample | Time range (min) | Monomer Content (%) | Dimer (%) | Tetramer (%) |
|---|---|---|---|---|
| Starting Material | — | 74.1 | 20.3 | 5.6 |
| Flow Through | 82-100 | 100 | 0 | 0 |
| Eluate 0 | 100-104 | 100 | 0 | 0 |
| Eluate 1 | 104-107 | 97.8 | 2.2 | 0 |
| Eluate 2 | 107-110 | 72.3 | 22.9 | 4.8 |
| Eluate 3 | 110-113 | 60.3 | 29.1 | 10.6 |
| Combined Eluates 0 to 2 | 100-110 | 83.6 | 13.6 | 2.8 |

Referring to Tables 7 and 8, prototype 13 resin gave better aggregate clearance efficiency as evidenced by early elution fractions containing high monomer content (i.e., there was monomer enrichment in the early elution fractions Eluate 0 and Eluate 1). The recovery results of mAb S with prototype 12 showed no significant difference in monomer content among the elution fractions; thus, no monomer enrichment was observed in the early elution fractions (Eluate 1 and Eluate 2).

Figure 4:
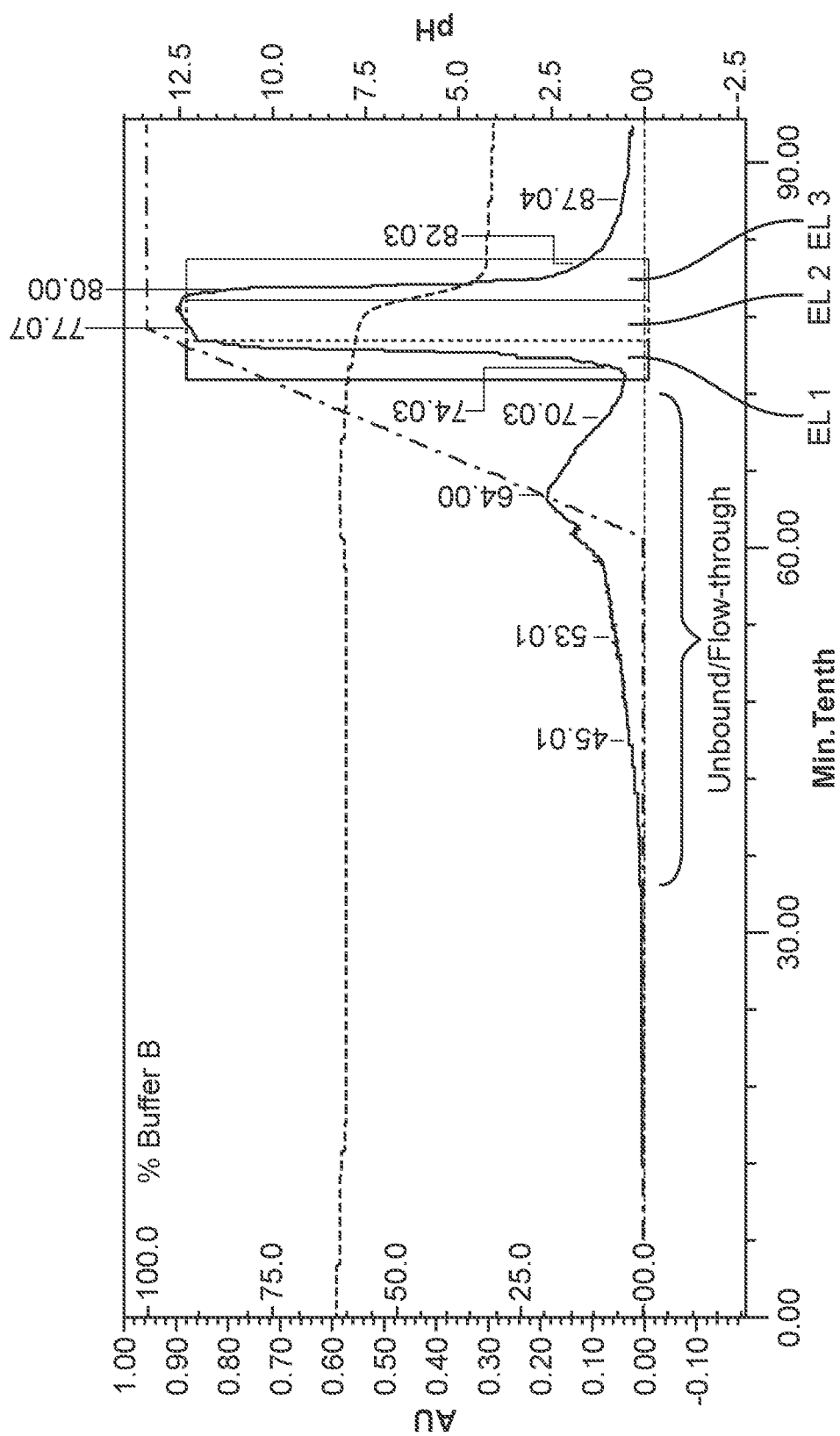
FIG. 4 is a bind-elute mode purification chromatogram of mAb S on Prototype 12.
Figure 5:
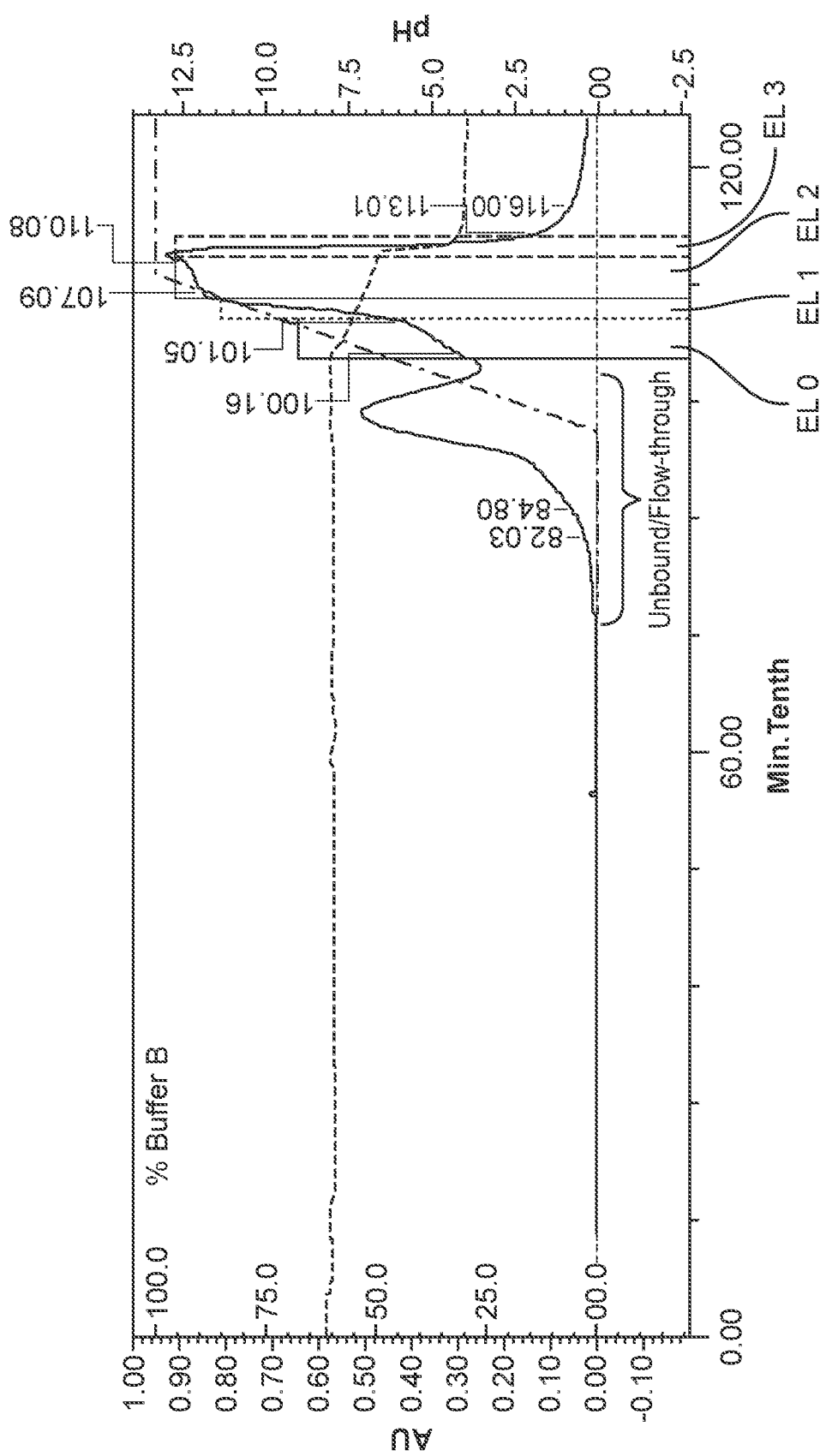
FIG. 5 is a bind-elute mode purification chromatogram of mAb S on Prototype 13.

FIGS. 4 and 5 are bind-elute mode purification chromatograms of mAb S on prototype 12 resin and prototype 13 resin, respectively. During purification, Absorbance Units (AU on the left y-axis) and pH (pH units are on the right y-axis) was monitored as a function of time. Referring to FIG. 4, as the pH decreased from 7.8 to 4, mAb S eluted from prototype 12 resin, but no enrichment in monomeric mAb S was observed in the elution fractions (as evidenced by the monomer content results in Table 7). Thus, for prototype 12 resin, a pH gradient from 7.8 to 4 did not result in purified mAb S. Referring to FIG. 5, as the pH decreased from 7.8 to 4, mAb S monomer was eluted from prototype 13 resin and elution of mAb S monomer was complete at about pH 6 (or during elution fraction Eluate 3). Given that elution of mAb S monomer was complete by elution fraction Eluate 3 and that monomer enrichment occurred in elution fractions Eluate 0 and Eluate 1 (as evidenced by the monomer content results in Table 8), pH 6 instead of pH 4 can be used to elute monomeric mAb S from prototype 13 resin. This is supported by the bind-elute results for mAb S with prototype 13 resin at pH 6 shown in Example 3.

All patents, patent applications, and other published reference materials cited in this specification are hereby incorporated herein by reference in their entirety.

Additional Disclosure and Claimable Subject Matter

Item 1. A chromatography resin having the following formula:

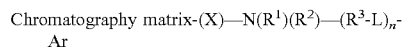

Chromatography matrix-(X)—N($R^1$)($R^2$)—($R^3$-L)$_n$-Ar or an anionic salt thereof,
wherein:
X is a spacer;
$R^1$ and $R^2$ are each independently $C_1$ to $C_6$ alkyl optionally substituted with —OH;
$R^3$ is $C_2$ to $C_6$ alkyl or $C_4$ to $C_6$ cycloalkyl;
L is $NR^4$, O, or S, wherein $R^4$ is hydrogen or $C_1$ to $C_4$ alkyl;
n is 1 or 2; and
Ar is a 6-10 membered ring and:
  if Ar is aryl, the aryl is optionally substituted with up to five $C_1$ to $C_3$ unsubstituted alkyl, $C_3$ to $C_6$ branched alkyl, unsubstituted aryl, or fluorine groups; or
  if Ar is heteroaryl, the heteroaryl is optionally substituted with up to four alkyl groups.

Item 2. The chromatography matrix of item 1, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—;
$R^1$ and $R^2$ are each independently $C_1$ to $C_3$ alkyl;
$R^3$ is $C_2$ to $C_4$ alkyl;
L is O;
n is 1; and
Ar is a 6 membered ring and:
  if Ar is aryl, the aryl is optionally substituted with up to four $C_1$ to $C_2$ unsubstituted alkyl, $C_3$ to $C_4$ branched alkyl, or fluorine groups or
  if Ar is heteroaryl, the heteroaryl is optionally substituted with up to three alkyl groups.

Item 3. The chromatography resin of item 2, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH($CH_2$—OH)—(O—$CH_2$—CH(OH)—$CH_2$)$_2$—;
$R^1$ and $R^2$ are each independently $C_1$ or $C_2$ alkyl;

$R^3$ is $C_2$ or $C_3$ alkyl;
L is O;
n is 1; and
Ar is phenyl, naphthyl, or pyridyl optionally substituted with up to three $C_1$ to $C_2$ unsubstituted alkyl.

Item 4. The chromatography resin of any one of items 1-3, wherein Ar is phenyl optionally substituted with one or two $C_1$ to $C_2$ unsubstituted alkyl.

Item 5. The chromatography resin of any one of items 1-4, wherein —(X)—N($R^1$)($R^2$)—($R^3$-L)$_n$-Ar is any one of the ligands of Table 1.

Item 6. A chromatography resin having the following formula:

$$\text{Chromatography matrix-(X)—N}(R^1)—[(R^3\text{-L})_n\text{-Ar}]_2$$

or an anionic salt thereof,
wherein:
X is a spacer;
$R^1$ is $C_1$ to $C_6$ alkyl optionally substituted with —OH;
$R^3$ is $C_2$ to $C_6$ alkyl or $C_4$ to $C_6$ cycloalkyl;
L is $NR^4$, O, or S, wherein $R^4$ is hydrogen or $C_1$ to $C_4$ alkyl;
n is 1 or 2; and
Ar is a 6-10 membered ring and:
  if Ar is aryl, the aryl is optionally substituted with up to four $C_1$ to $C_3$ unsubstituted alkyl, $C_3$ to $C_6$ branched alkyl, unsubstituted aryl, or fluorine groups; or
  if Ar is heteroaryl, the heteroaryl is optionally substituted with up to four alkyl groups.

Item 7. The chromatography resin of item 6, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, —O—$CH_2$—CH($CH_2$—OH)—(O—$CH_2$—CH(OH)—$CH_2$)$_2$—, —O—$CH_2$—$CH_2$—CH($CH_2$—OH)—(O—$CH_2$—$CH_2$—CH(OH)—$CH_2$)$_2$—, —O—$CH_2$—CH(OH)—$CH_2$—, —O—$CH_2$—$CH_2$—CH(OH)—$CH_2$—$CH_2$—, —O—$CH_2$—CH(OH)—$CH_2$—O—$CH_2$—$CH_2$—$CH_2$—$CH_2$—O—$CH_2$—CH(OH)—$CH_2$—, and —CO—NH—C($CH_3$)$_2$—CO—;
$R^1$ is $C_1$ to $C_3$ alkyl;
$R^3$ is $C_2$ to $C_4$ alkyl;
L is O;
n is 1; and
Ar is a 6 membered ring and:
  if Ar is aryl, the aryl is optionally substituted with up to four $C_1$ to $C_2$ unsubstituted alkyl, $C_3$ to $C_4$ branched alkyl, or fluorine groups or
  if Ar is heteroaryl, the heteroaryl is optionally substituted with up to three alkyl groups.

Item 8. The chromatography resin of item 7, wherein:
X is selected from the group consisting of —O—$CH_2$—, —O—$CH_2$—$CH_2$—, —O—$CH_2$—$CH_2$—$CH_2$—, —O—$CH_2$—$CH_2$—$CH_2$—$CH_2$—, and —O—$CH_2$—CH($CH_2$—OH)—(O—$CH_2$—CH(OH)—$CH_2$)$_2$—;
$R^1$ is $C_1$ or $C_2$ alkyl;
$R^3$ is $C_2$ or $C_3$ alkyl; and
L is O;
n is 1; and
Ar is phenyl, naphthyl, or pyridyl optionally substituted with up to three $C_1$ to $C_2$ unsubstituted alkyl.

Item 9. The chromatography resin of any one of items 6-8, wherein Ar is phenyl optionally substituted with one or two $C_1$ to $C_2$ unsubstituted alkyl.

Item 10. The chromatography resin of any one of items 6-9, wherein —(X)—N($R^1$)—[($R^3$-L)$_n$-Ar] is any one of the ligands of Table 2.

Item 11. The chromatography resin of any one of items 1-10, wherein Ar is unsubstituted.

Item 12. The chromatography resin of item 1 or 6, wherein Ar is heteroaryl and a heteroatom in the heteroaryl is N.

Item 13. The chromatography resin of any one of items 1-12, wherein the anionic salt is a hydrochloride salt or a sulfate salt.

Item 14. The chromatography resin of any one of items 1-13, wherein X is attached to chromatography matrix via an amine, ether or amide bond.

Item 15. A chromatography resin prepared by reacting any one of the ligands of Table 1 with a chromatography matrix by any one of reductive amination, epoxide chemistry, or azalactone chemistry.

Item 16. The chromatography resin of item 15, wherein the chromatography matrix comprises an aldehyde group and any one of the ligands of Table 1 is reacted with the chromatography matrix by reductive amination.

Item 17. The chromatography resin of item 15, wherein the chromatography matrix comprises an epoxide group and any one of the ligands of Table 1 is reacted with the chromatography matrix by epoxide chemistry.

Item 18. The chromatography resin of any one of items 15-17 wherein prior to reacting the chromatography matrix with the ligand, the chromatography matrix is reacted with allylglydicylether and bromine; 1,4-butanedioldiglycidyl; or epichlorohydrin.

Item 19. The chromatography resin of item 18, wherein the chromatography matrix comprises a —OH group and is reacted with allylglydicylether and bromine.

Item 20. A chromatography resin prepared by reacting any one of the ligands of Table 2 with a chromatography matrix by epoxide chemistry.

Item 21. A method of purifying a biomolecule, the method comprising:
contacting a sample comprising the biomolecule to a chromatography resin of any one of items 1-20, thereby separating the biomolecule from a contaminant; and
collecting a purified biomolecule.

Item 22. The method of item 21, wherein the purified biomolecule is a protein.

Item 23. The method of item 22, wherein the protein is an antibody.

Item 24. The method of any one of items 21-23, wherein the sample comprises a monomeric antibody and antibody aggregates, the method comprises separating the monomeric antibody from the antibody aggregates, and the purified biomolecule comprises the monomeric antibody.

Item 25. The method of any one of items 24, wherein the purified biomolecule is a monomeric antibody.

Item 26. The method of item 25, wherein the contacting step comprises immobilizing the monomeric antibody to the chromatography matrix and the collecting step comprises eluting the monomeric antibody from the chromatography matrix.

Item 27. The method of item 26, wherein the monomeric antibody is eluted by a step comprising reducing a pH of a solution in contact with the ligand from about 7-9 to about 4-6.

Item 28. The method of item 25, wherein the contacting step comprises flowing the monomeric antibody through the chromatography matrix and the collecting step comprises collecting the monomeric antibody in the flow through.

The invention claimed is:

1. A chromatography resin having the following formula:

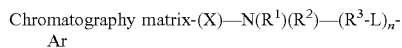

or an anionic salt thereof,
wherein:
X is a spacer from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, —O—CH$_2$—CH(CH$_2$—OH)—(O—CH$_2$—CH(OH)—CH$_2$)$_2$—, —O—CH$_2$—CH$_2$—CH(CH$_2$—OH)—(O—CH$_2$—CH(OH)—CH$_2$)$_2$—, —O—CH$_2$—CH(OH)—CH$_2$—, —O—CH$_2$—CH$_2$—CH(OH)—CH$_2$—CH$_2$—, —O—CH$_2$—CH(OH)—CH$_2$—O—CH$_2$—CH$_2$—CH$_2$—CH$_2$—O—CH$_2$—CH(OH)—CH$_2$—, and —CO—NH—C(CH$_3$)$_2$—CO—;
R$^1$ and R$^2$ are each independently C$_1$ to C$_6$ alkyl optionally substituted with —OH;
R$^3$ is C$_2$ to C$_6$ alkyl or C$_4$ to C$_6$ cycloalkyl;
L is O;
n is 1 or 2; and
Ar is a phenyl or naphthyl group optionally substituted with up to 5: C$_1$ to C$_3$ unsubstituted alkyl, C$_3$ to C$_6$ branched alkyl, unsubstituted aryl, or flourine groups; or
a pyridal group optionally substituted with up to four alkyl groups.

2. The chromatography matrix of claim 1, wherein:
R$^1$ and R$^2$ are each independently C$_1$ to C$_3$ alkyl;
R$^3$ is C$_2$ to C$_4$ alkyl;
L is O;
n is 1; and
Ar is a phenyl or naphthyl group optionally substituted with up to four C$_1$ to C$_2$ unsubstituted alkyl, C$_3$ to C$_4$ branched alkyl, or flourine groups; or
a pyridal group optionally substituted with up to three alkyl groups.

3. The chromatography resin of claim 1, wherein:
X is selected from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, and —O—CH$_2$—CH(CH$_2$—OH)—(O—CH$_2$—CH(OH)—CH$_2$)$_2$—;
R$^1$ and R$^2$ are each independently C$_1$ or C$_2$ alkyl;
R$^3$ is C$_2$ or C$_3$ alkyl;
L is O;
n is 1; and
Ar is phenyl, naphthyl, or pyridyl optionally substituted with up to three C$_1$ to C$_2$ unsubstituted alkyl.

4. The chromatography resin of claim 1, wherein Ar is phenyl optionally substituted with one or two C$_1$ to C$_2$ unsubstituted alkyl.

5. The chromatography resin of claim 1, wherein the chromatography resin has one of the following structures, the sphere representing the chromatography matrix and the spacer X:

| | Resin Number |
|---|---|
| 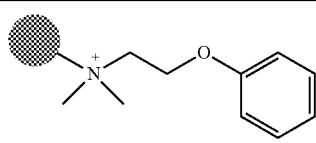 | 13 |
| 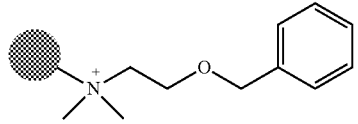 | 94 |
| 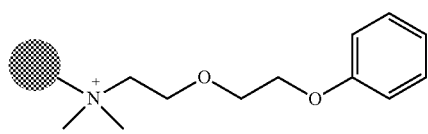 | 34-1 |
| 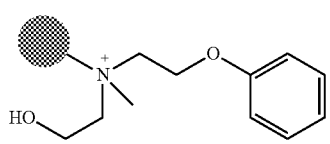 | 34-2 |
| 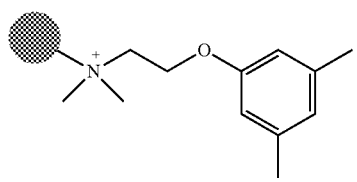 | 86-1 |
| 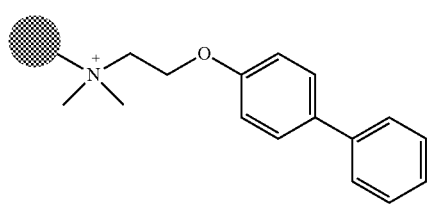 | 86-2 |
| 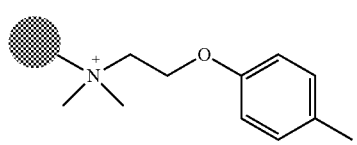 | 97-1 |
| 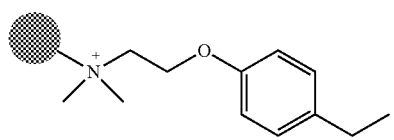 | 97-2 |
| 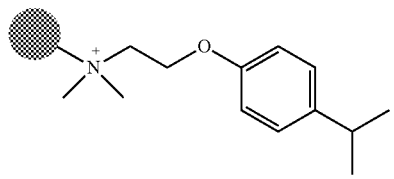 | 98-1 |
| 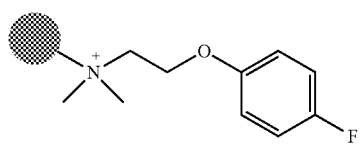 | 32-1 |

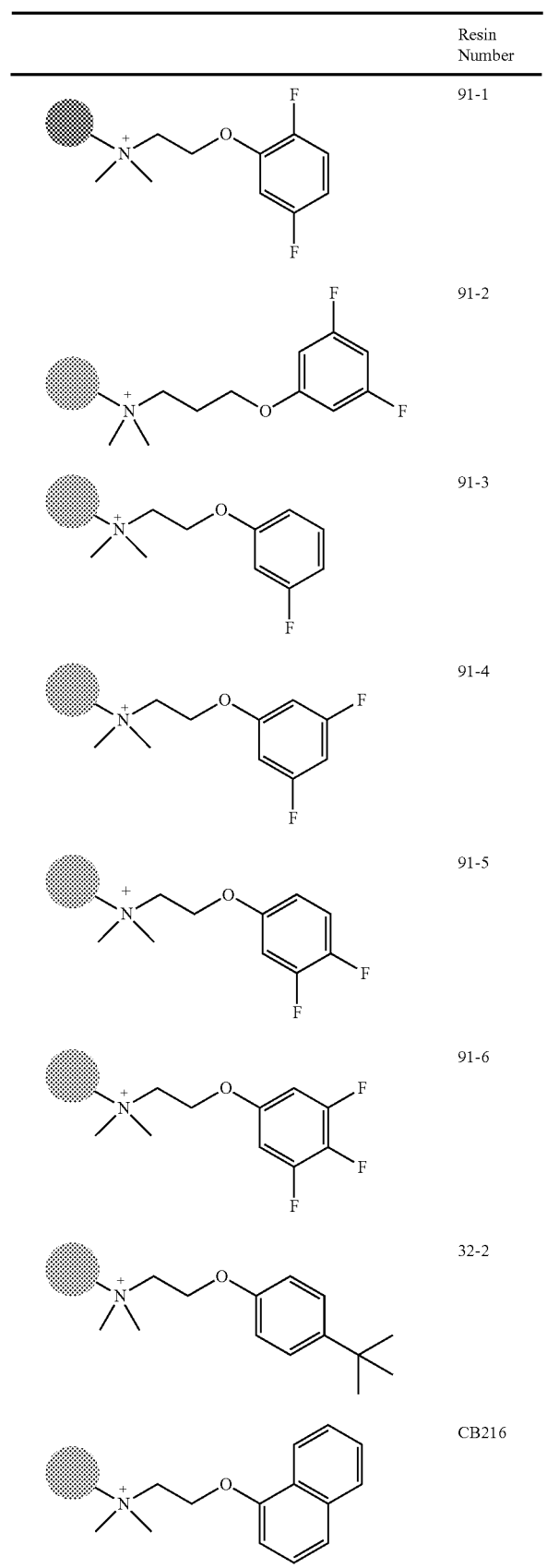
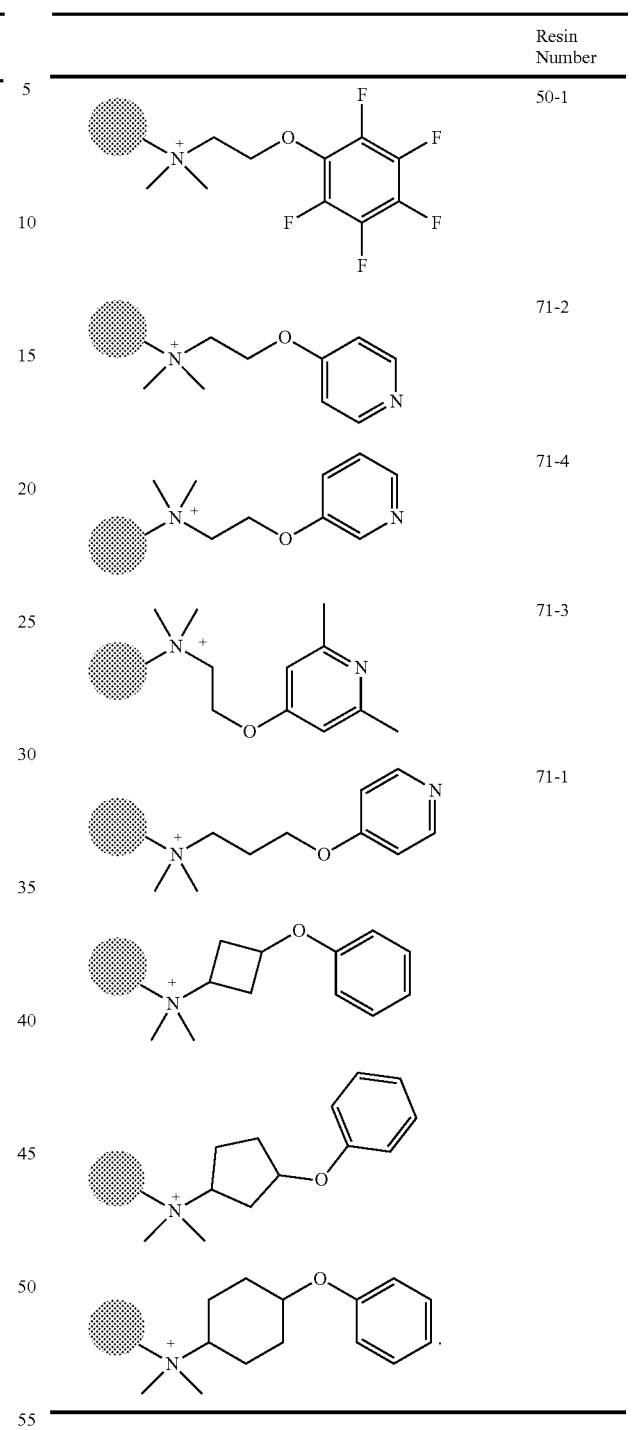

6. The chromatography resin of claim 1, wherein Ar is unsubstituted.

7. The chromatography resin of claim 1, wherein Ar is a pyridyl group optionally substituted with up to four alkyl groups.

8. The chromatography resin of claim 1, wherein the anionic salt is a hydrochloride salt or a sulfate salt.

9. The chromatography resin of claim 1, wherein X is attached to chromatography matrix via an amine, ether or amide bond.

10. A chromatography resin having the following formula:

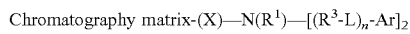

or an anionic salt thereof,
wherein:
X is a spacer from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, —O—CH$_2$—CH(CH$_2$—OH)—(O—CH$_2$—CH(OH)—CH$_2$)$_2$—, —O—CH$_2$—CH$_2$—CH(CH$_2$—OH)—(O—CH$_2$—CH$_2$—CH(OH)—CH$_2$)$_2$—, —O—CH$_2$—CH(OH)—CH$_2$—, —O—CH$_2$—CH$_2$—CH(OH)—CH$_2$—CH$_2$—, —O—CH$_2$—CH(OH)—CH$_2$—O—CH$_2$—CH$_2$—CH$_2$—CH$_2$—O—CH$_2$—CH(OH)—CH$_2$—, and —CO—NH—C(CH$_3$)$_2$—CO—;
R$^1$ is C$_1$ to C$_6$ alkyl optionally substituted with —OH;
R$^3$ is C$_2$ to C$_6$ alkyl or C$_4$ to C$_6$ cycloalkyl;
L is O;
n is 1; and
Ar is a phenyl or naphthyl group optionally substituted with up to 5: C$_1$ to C$_3$ unsubstituted alkyl, C$_3$ to C$_6$ branched alkyl, unsubstituted aryl, or flourine groups; or
a pyridal group optionally substituted with up to four alkyl groups.

11. The chromatography resin of claim 10, wherein:
X is selected from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, —O—CH$_2$—CH(CH$_2$—OH)—(O—CH$_2$—CH(OH)—CH$_2$)$_2$—, —O—CH$_2$—CH$_2$—CH(CH$_2$—OH)—(O—CH$_2$—CH$_2$—CH(OH)—CH$_2$)$_2$—, —O—CH$_2$—CH(OH)—CH$_2$—, —O—CH$_2$—CH$_2$—CH(OH)—CH$_2$—CH$_2$—, —CH$_2$—CH(OH)—CH$_2$—O—CH$_2$—CH$_2$—CH$_2$—CH$_2$—O—CH$_2$—CH(OH)—CH$_2$—, and —CO—NH—C(CH$_3$)$_2$—CO—;
R$^1$ is C$_1$ to C$_3$ alkyl;
R$^3$ is C$_2$ to C$_4$ alkyl;
L is O;
n is 1; and
L is O;
n is 1; and
Ar is a phenyl or naphthyl group optionally substituted with up to four C$_1$ to C$_2$ unsubstituted alkyl, C$_3$ to C$_4$ branched alkyl, or flourine groups; or
a pyridal group optionally substituted with up to three alkyl groups.

12. The chromatography resin of claim 11, wherein:
X is selected from the group consisting of —O—CH$_2$—, —O—CH$_2$—CH$_2$—, —O—CH$_2$—CH$_2$—CH$_2$—, —O—CH$_2$—CH$_2$—CH$_2$—CH$_2$—, and —O—CH$_2$—CH(CH$_2$—OH)—(O—CH$_2$—CH(OH)—CH$_2$)$_2$—;
R$^1$ is C$_1$ or C$_2$ alkyl;
R$^3$ is C$_2$ or C$_3$ alkyl; and
L is O;
n is 1; and
Ar is phenyl, naphthyl, or pyridyl optionally substituted with up to three C$_1$ to C$_2$ unsubstituted alkyl.

13. The chromatography resin of claim 10, wherein Ar is phenyl optionally substituted with one or two C$_1$ to C$_2$ unsubstituted alkyl.

14. The chromatography resin of claim 10, wherein the chromatography resin has one of the following structures, the sphere representing the chromatography matrix and the spacer X:

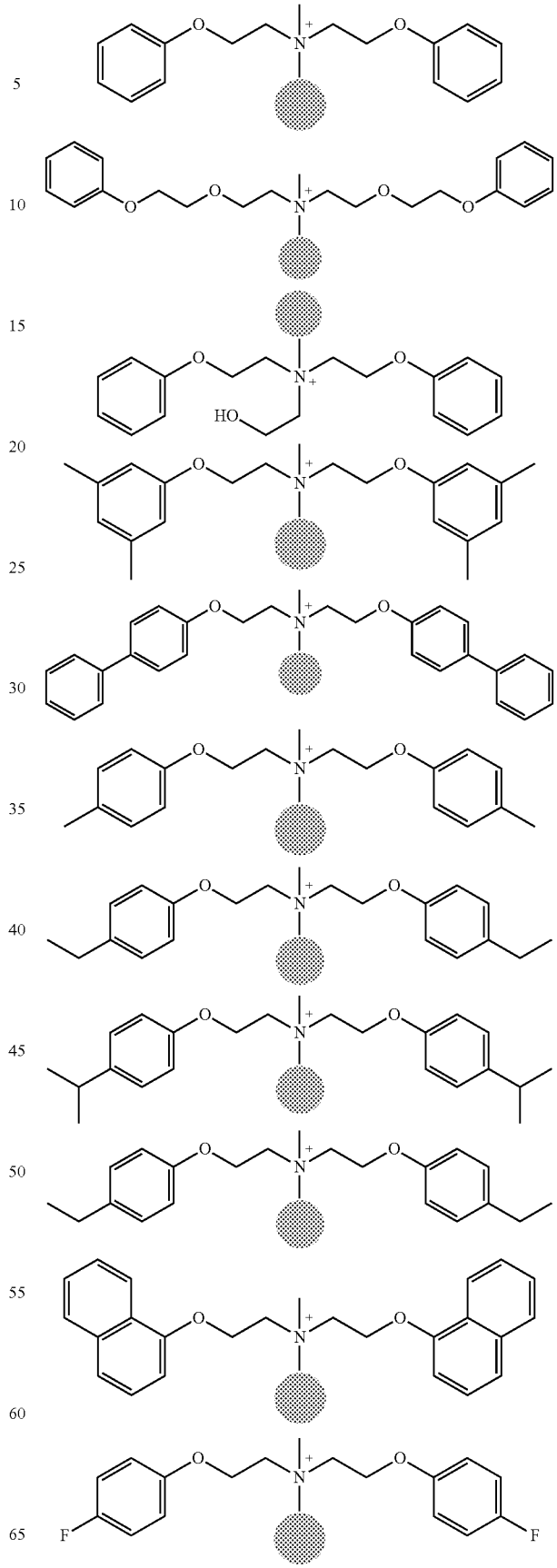

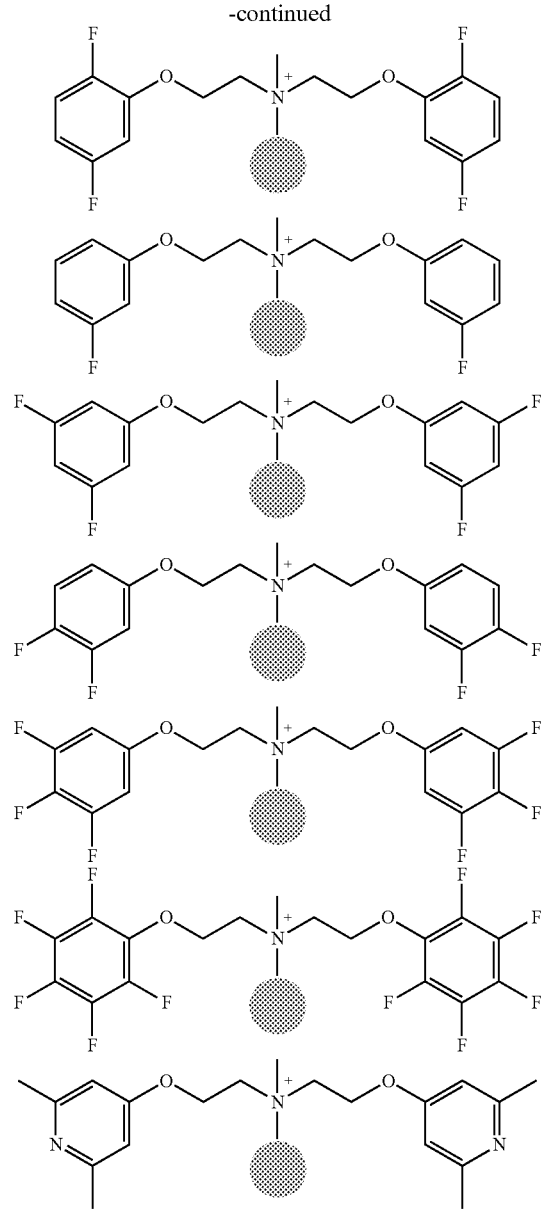
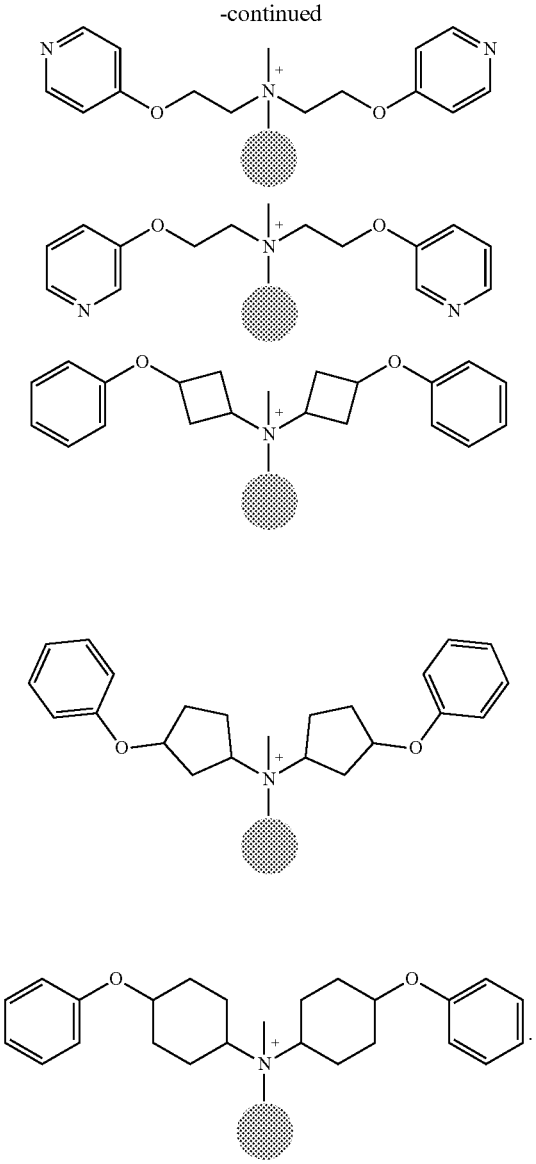
* * * * *